(12) United States Patent
Lahm et al.

(10) Patent No.: US 10,820,590 B2
(45) Date of Patent: Nov. 3, 2020

(54) NEMATOCIDAL HETEROCYCLIC AMIDES

(71) Applicant: E I DU PONT DE NEMOURS AND COMPANY, Wilmington, DE (US)

(72) Inventors: George Philip Lahm, Wilmington, DE (US); Andrew Jon Deangelis, Wilmington, DE (US); Matthew James Campbell, Rising Sun, MD (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 116 days.

(21) Appl. No.: 16/067,410

(22) PCT Filed: Dec. 8, 2016

(86) PCT No.: PCT/US2016/065580
§ 371 (c)(1),
(2) Date: Jun. 29, 2018

(87) PCT Pub. No.: WO2017/116646
PCT Pub. Date: Jul. 6, 2017

(65) Prior Publication Data
US 2019/0014779 A1 Jan. 17, 2019

Related U.S. Application Data

(60) Provisional application No. 62/353,795, filed on Jun. 23, 2016, provisional application No. 62/272,728, filed on Dec. 30, 2015.

(51) Int. Cl.
A01N 43/08 (2006.01)
A01N 43/10 (2006.01)
A01N 43/78 (2006.01)
C07D 333/38 (2006.01)
C07D 277/56 (2006.01)
C07D 307/08 (2006.01)
C07D 307/68 (2006.01)

(52) U.S. Cl.
CPC ............ A01N 43/08 (2013.01); A01N 43/10 (2013.01); A01N 43/78 (2013.01); C07D 277/56 (2013.01); C07D 307/08 (2013.01); C07D 307/68 (2013.01); C07D 333/38 (2013.01)

(58) Field of Classification Search
None
See application file for complete search history.

(56) References Cited

FOREIGN PATENT DOCUMENTS

WO WO-2007039615 A1 * 4/2007 ............ C07D 307/54

OTHER PUBLICATIONS

Shinzo Kagabu, et al.; Stability Comparison of Imidacloprid and Related Compounds under Simulated Sunlight, Hydrolysis Conditions, and to Oxygen; 1995; pp. 980-985; Biosci. Biotech. Biochem., 59 (6); Gifu 501-11, Japan.

Shinzo Kagabu, et al.; Insecticidal and Neuroblocking Activites of Thiamethoxam-Type Compounds in the American Cockroach (*Periplaneta americana* L.); 2005; pp. 111-115; J. Pestic. Sci., 30 (2); Gifu 501-1193, Japan.

Yasushi Shiga, et al.; Synthesis and Acaricidal Activity of N-(1,3,4-Thiadiazol-2-yl)cyclopropanecarboxamides; 2003; pp. 61-63; J. Pesticide Sci., 28; Kanagawa 227-8502, Japan.

Takeo Wakita, et al.; Synthesis and Structure-Activity Relationships of Dinotefuran Derivatives: Modification in the Tetrahydro-3-furylmethyl Part; 2004; pp. 356-363; J. Pestic. Sci., 29(40); Chiba 297-0017, Japan.

* cited by examiner

*Primary Examiner* — Alton N Pryor

(57) ABSTRACT

Disclosed are compounds of Formulae 1, 1a, 1b and 2,

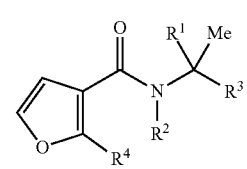

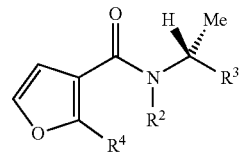

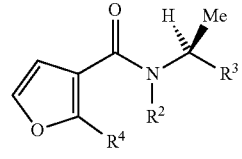

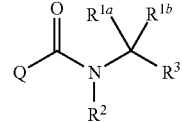

wherein
$R^1$, $R^{1a}$, $R^{1b}$, $R^2$, $R^3$ and $R^4$ are as defined in the disclosure.

Also disclosed are compositions containing the compounds of Formulae 1, 1a and 1b, and methods for controlling a parasitic nematode comprising contacting the parasitic nematode or its environment with a biologically effective amount of a compound or composition of Formulae 1, 1a, 1b and 2.

10 Claims, No Drawings

NEMATOCIDAL HETEROCYCLIC AMIDES

FIELD OF THE INVENTION

This invention relates to certain heterocyclic amides and their compositions suitable for agronomic and nonagronomic uses, and methods of their use for controlling parasitic nematodes in both agronomic and nonagronomic environments.

BACKGROUND OF THE INVENTION

The control of plant-parasitic nematodes is extremely important in achieving high crop efficiency. Nematode-induced root damage can cause significant reduction in crop yields and quality and thereby result in increased costs to the consumer. Due to widespread development of resistance to anthelmintic agents in nematode parasites, nematodes continue to cause problems in livestock despite the available chemical therapeutic agents. The need continues for new compounds which are more effective, less costly, less toxic, environmentally safer or have different modes of action.

SUMMARY OF THE INVENTION

This invention is directed to compounds of Formula 1 (including all stereoisomers) and compositions containing them and their use for controlling a parasitic nematode:

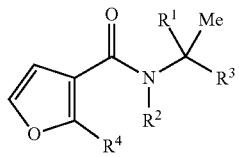

1 wherein
- $R^1$ is H or methyl;
- $R^2$ is H; or $C_1$-$C_6$ alkyl, $C_2$-$C_6$ alkenyl, $C_2$-$C_6$ alkynyl, $C_3$-$C_6$ cycloalkyl, $C_2$-$C_6$ alkylcarbonyl, $C_2$-$C_6$ alkoxycarbonyl, $C_1$-$C_6$ alkylthio or $C_1$-$C_6$ alkylsulfonyl, each unsubstituted or substituted with at least one $R^5$;
- $R^3$ is $C_2$-$C_{16}$ alkyl, $C_2$-$C_{16}$ alkenyl, $C_2$-$C_{16}$ alkynyl or $C_3$-$C_6$ cycloalkyl, each unsubstituted or substituted with at least one $R^6$;
- $R^4$ is Cl or Br;
- each $R^5$ is independently halogen, cyano, $C_1$-$C_3$ alkoxy, $C_3$-$C_6$ cycloalkyl, $C_1$-$C_3$ alkylthio, $C_1$-$C_3$ alkylsulfinyl or $C_1$-$C_3$ alkylsulfonyl;
- each $R^6$ is independently halogen, cyano, $C_1$-$C_3$ alkoxy, $C_3$-$C_6$ cycloalkyl, $C_1$-$C_3$ alkylthio, $C_1$-$C_3$ alkylsulfinyl, $C_1$-$C_3$ alkylsulfonyl or $SiR^aR^bR^c$; and
- each $R^a$, $R^b$ and $R^c$ is independently $C_1$-$C_6$ alkyl;
- provided that (i) when $R^1$ and $R^2$ are H, then $R^3$ is other than $C_2$-$C_3$ alkenyl, $C_2$-$C_3$ alkynyl, cyclopropyl, —CH$_2$OCH$_3$, —CH$_2$SCH$_3$, unsubstituted $C_2$-$C_3$ alkyl, or $C_2$-$C_3$ alkyl substituted with Cl or Br; (ii) when $R^1$ is methyl, then $R^3$ is other than ethyl; and (iii) when $R^1$ is H and $R^2$ is methyl, then $R^3$ is other than ethyl.

This invention is also directed to compounds of Formula 1a and compositions containing them and their use for controlling a parasitic nematode:

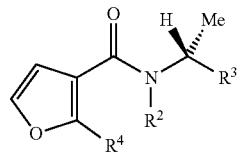

1a wherein
- $R^2$ is H; or $C_1$-$C_6$ alkyl, $C_2$-$C_6$ alkenyl, $C_2$-$C_6$ alkynyl, $C_3$-$C_6$ cycloalkyl, $C_2$-$C_6$ alkylcarbonyl, $C_2$-$C_6$ alkoxycarbonyl, $C_1$-$C_6$ alkylthio or $C_1$-$C_6$ alkylsulfonyl, each unsubstituted or substituted with at least one $R^5$;
- $R^3$ is $C_2$-$C_{16}$ alkyl, $C_2$-$C_{16}$ alkenyl, $C_2$-$C_{16}$ alkynyl or $C_3$-$C_6$ cycloalkyl, each unsubstituted or substituted with at least one $R^6$;
- $R^4$ is Cl, Br, I, CH$_3$, CF$_3$ or cyano;
- each $R^5$ is independently halogen, cyano, $C_1$-$C_3$ alkoxy, $C_3$-$C_6$ cycloalkyl, $C_1$-$C_3$ alkylthio, $C_1$-$C_3$ alkylsulfinyl or $C_1$-$C_3$ alkylsulfonyl;
- each $R^6$ is independently halogen, cyano, $C_1$-$C_3$ alkoxy, $C_3$-$C_6$ cycloalkyl, $C_1$-$C_3$ alkylthio, $C_1$-$C_3$ alkylsulfinyl, $C_1$-$C_3$ alkylsulfonyl or $SiR^aR^bR^c$; and
- each $R^a$, $R^b$ and $R^c$ is independently $C_1$-$C_6$ alkyl.

This invention is also directed to compounds of Formula 1a and compositions containing them and their use for controlling a parasitic nematode:

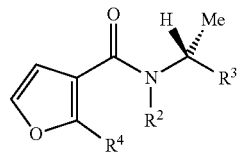

1a wherein
- $R^2$ is H; or $C_1$-$C_6$ alkyl, $C_2$-$C_6$ alkenyl, $C_2$-$C_6$ alkynyl, $C_3$-$C_6$ cycloalkyl, $C_2$-$C_6$ alkylcarbonyl, $C_2$-$C_6$ alkoxycarbonyl, $C_1$-$C_6$ alkylthio or $C_1$-$C_6$ alkylsulfonyl, each unsubstituted or substituted with at least one $R^5$;
- $R^3$ is $C_2$-$C_{16}$ alkyl, $C_2$-$C_{16}$ alkenyl, $C_2$-$C_{16}$ alkynyl or $C_3$-$C_6$ cycloalkyl, each unsubstituted or substituted with at least one $R^6$;
- $R^4$ is Cl, Br, I, CH$_3$, CF$_3$ or cyano;
- each $R^5$ is independently halogen, cyano, $C_1$-$C_3$ alkoxy, $C_3$-$C_6$ cycloalkyl, $C_1$-$C_3$ alkylthio, $C_1$-$C_3$ alkylsulfinyl or $C_1$-$C_3$ alkylsulfonyl;
- each $R^6$ is independently halogen, cyano, $C_1$-$C_3$ alkoxy, $C_3$-$C_6$ cycloalkyl, $C_1$-$C_3$ alkylthio, $C_1$-$C_3$ alkylsulfinyl, $C_1$-$C_3$ alkylsulfonyl or $SiR^aR^bR^c$; and
- each $R^a$, $R^b$ and $R^c$ is independently $C_1$-$C_6$ alkyl;
- provided that (i) when $R^2$ is H, then $R^3$ is other than $C_2$-$C_3$ alkenyl, $C_2$-$C_3$ alkynyl, cyclopropyl, —CH$_2$OCH$_3$, —CH$_2$SCH$_3$, unsubstituted $C_2$-$C_3$ alkyl, or $C_2$-$C_3$ alkyl substituted with Cl or Br; and (ii) when $R^2$ is methyl, then $R^3$ is other than ethyl.

This invention is also directed to compounds of Formula 1b and compositions containing them and their use for controlling a parasitic nematode:

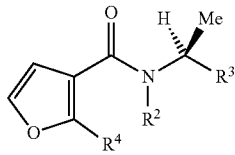

wherein
R$^2$ is H; or C$_1$-C$_6$ alkyl, C$_2$-C$_6$ alkenyl, C$_2$-C$_6$ alkynyl, C$_3$-C$_6$ cycloalkyl, C$_2$-C$_6$ alkylcarbonyl, C$_2$-C$_6$ alkoxycarbonyl, C$_1$-C$_6$ alkylthio or C$_1$-C$_6$ alkylsulfonyl, each unsubstituted or substituted with at least one R$^5$;
R$^3$ is C$_2$-C$_{16}$ alkyl, C$_2$-C$_{16}$ alkenyl, C$_2$-C$_{16}$ alkynyl or C$_3$-C$_6$ cycloalkyl, each unsubstituted or substituted with at least one R$^6$;
R$^4$ is Cl, Br, I, CH$_3$, CF$_3$ or cyano;
each R$^5$ is independently halogen, cyano, C$_1$-C$_3$ alkoxy, C$_3$-C$_6$ cycloalkyl, C$_1$-C$_3$ alkylthio, C$_1$-C$_3$ alkylsulfinyl or C$_1$-C$_3$ alkylsulfonyl;
each R$^6$ is independently halogen, cyano, C$_1$-C$_3$ alkoxy, C$_3$-C$_6$ cycloalkyl, C$_1$-C$_3$ alkylthio, C$_1$-C$_3$ alkylsulfinyl, C$_1$-C$_3$ alkylsulfonyl or SiR$^a$R$^b$R$^c$; and
each R$^a$, R$^b$ and R$^c$ is independently C$_1$-C$_6$ alkyl.

This invention is also directed to compounds of Formula 1b and compositions containing them and their use for controlling a parasitic nematode:

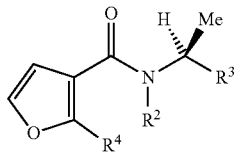

wherein
R$^2$ is H; or C$_1$-C$_6$ alkyl, C$_2$-C$_6$ alkenyl, C$_2$-C$_6$ alkynyl, C$_3$-C$_6$ cycloalkyl, C$_2$-C$_6$ alkylcarbonyl, C$_2$-C$_6$ alkoxycarbonyl, C$_1$-C$_6$ alkylthio or C$_1$-C$_6$ alkylsulfonyl, each unsubstituted or substituted with at least one R$^5$;
R$^3$ is C$_2$-C$_{16}$ alkyl, C$_2$-C$_{16}$ alkenyl, C$_2$-C$_{16}$ alkynyl or C$_3$-C$_6$ cycloalkyl, each unsubstituted or substituted with at least one R$^6$;
R$^4$ is Cl, Br, I, CH$_3$, CF$_3$ or cyano;
each R$^5$ is independently halogen, cyano, C$_1$-C$_3$ alkoxy, C$_3$-C$_6$ cycloalkyl, C$_1$-C$_3$ alkylthio, C$_1$-C$_3$ alkylsulfinyl or C$_1$-C$_3$ alkylsulfonyl;
each R$^6$ is independently halogen, cyano, C$_1$-C$_3$ alkoxy, C$_3$-C$_6$ cycloalkyl, C$_1$-C$_3$ alkylthio, C$_1$-C$_3$ alkylsulfinyl, C$_1$-C$_3$ alkylsulfonyl or SiR$^a$R$^b$R$^c$; and
each R$^a$, R$^b$ and R$^c$ is independently C$_1$-C$_6$ alkyl;
provided that (i) when R$^2$ is H, then R$^3$ is other than C$_2$-C$_3$ alkenyl, C$_2$-C$_3$ alkynyl, cyclopropyl, —CH$_2$OCH$_3$, —CH$_2$SCH$_3$, unsubstituted C$_2$-C$_3$ alkyl, or C$_2$-C$_3$ alkyl substituted with Cl or Br; and (ii) when R$^2$ is methyl, then R$^3$ is other than ethyl.

This invention also provides a composition comprising a compound of Formula 1, 1a or 1b, and at least one additional component selected from the group consisting of surfactants, solid diluents and liquid diluents. In one embodiment, this invention also provides a composition for controlling a parasitic nematode comprising a compound of Formula 1, 1a or 1b and at least one additional component selected from the group consisting of surfactants, solid diluents and liquid diluents, said composition optionally further comprising at least one additional biologically active compound or agent.

This invention provides a method for controlling a parasitic nematode comprising contacting the parasitic nematode or its environment with a biologically effective amount of a compound of Formula 1, 1a or 1b (e.g., as a composition described herein). This invention also relates to such method wherein the parasitic nematode or its environment is contacted with a composition comprising a biologically effective amount of a compound of Formula 1, 1a or 1b, and at least one additional component selected from the group consisting of surfactants, solid diluents and liquid diluents, said composition optionally further comprising a biologically effective amount of at least one additional biologically active compound or agent.

This invention also provides a method for protecting a seed from a parasitic nematode comprising contacting the seed with a biologically effective amount of a compound of Formula 1, 1a or 1b (e.g., as a composition described herein). This invention also relates to the treated seed.

This invention also provides a method for controlling a parasitic nematode comprising contacting the parasitic nematode or its environment with a biologically effective amount of a compound of Formula 2

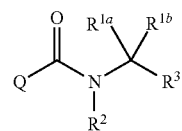

wherein
Q is a furan, thiophene or thiazole ring substituted with R$^4$ at a carbon atom adjacent to the carbon atom through which the furan, thiophene or thiazole ring is bonded to the remainder of Formula 2;
R$^{1a}$ is C$_1$-C$_6$ alkyl or C$_3$-C$_6$ cycloalkyl, each unsubstituted or substituted with at least one R$^5$;
R$^{1b}$ is H or C$_1$-C$_3$ alkyl; or
R$^{1a}$ and R$^{1b}$ are taken together with the carbon atom to which they are attached to form a 3- to 6-membered cycloalkyl ring, unsubstituted or substituted with at least one R$^5$;
R$^2$ is H; or C$_1$-C$_6$ alkyl, C$_2$-C$_6$ alkenyl, C$_2$-C$_6$ alkynyl, C$_3$-C$_6$ cycloalkyl, C$_2$-C$_6$ alkylcarbonyl, C$_2$-C$_6$ alkoxycarbonyl, C$_1$-C$_6$ alkylthio or C$_1$-C$_6$ alkylsulfonyl, each unsubstituted or substituted with at least one R$^5$;
R$^3$ is C$_2$-C$_{16}$ alkyl, C$_2$-C$_{16}$ alkenyl, C$_2$-C$_{16}$ alkynyl or C$_3$-C$_6$ cycloalkyl, each unsubstituted or substituted with at least one R$^6$;
R$^4$ is Cl, Br, I, CH$_3$, CF$_3$ or cyano; provided that when R$^4$ is Me, then R$^3$ is other than unsubstituted C$_2$ alkyl;
each R$^5$ is independently halogen, cyano, C$_1$-C$_3$ alkoxy, C$_3$-C$_6$ cycloalkyl, C$_1$-C$_3$ alkylthio, C$_1$-C$_3$ alkylsulfinyl, or C$_1$-C$_3$ alkylsulfonyl;
each R$^6$ is independently halogen, cyano, C$_1$-C$_3$ alkoxy, C$_3$-C$_6$ cycloalkyl, C$_1$-C$_3$ alkylthio, C$_1$-C$_3$ alkylsulfinyl, C$_1$-C$_3$ alkylsulfonyl or SiR$^a$R$^b$R$^c$; and
each R$^a$, R$^b$ and R$^c$ is independently C$_1$-C$_6$ alkyl.

This invention also relates to such method wherein the parasitic nematode or its environment is contacted with a composition comprising a biologically effective amount of a compound of Formula 2 and at least one additional component selected from the group consisting of surfactants, solid diluents and liquid diluents, said composition optionally further comprising a biologically effective amount of at least one additional biologically active compound or agent.

This invention also provides a method for protecting a seed from a parasitic nematode comprising contacting the seed with a biologically effective amount of a compound of Formula 2 (e.g., as a composition described herein). This invention also relates to the treated seed.

DETAILS OF THE INVENTION

As used herein, the terms "comprises", "comprising", "includes", "including", "has", "having", "contains", "containing", "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components or elements, in addition to those literally disclosed, provided that these additional materials, steps, features, components or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising", it should be readily understood that (unless otherwise stated) the description should be interpreted to also describe such an invention using the terms "consisting essentially of" or "consisting of".

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As used to in the present disclosure and claims, the term "nematode" refers to a living organism of the Phylum Nematoda. As generally defined, a "parasite" lives or grows inside or feeds on another living organism (such as a plant, animal or human) described as the "host". As referred to in the present disclosure and claims a "parasitic nematode" is particularly a nematode that injures or damages tissue or causes other forms of disease in plants, animals (particularly vertebrates) or humans.

A parasite "infestation" refers to the presence of parasites in numbers that pose a risk to plants, humans or animals. The presence can be in the environment, e.g., in a human or animal house, or surrounding property or structures, on an agricultural crop or other type of plant, in animal bedding, on the skin or fur of an animal, etc. When the infestation that is referred to is within an animal, e.g., in the blood or other internal tissues, the term infestation is also intended to be synonymous with the term, "infection," as that term is generally understood in the art, unless otherwise stated.

As referred to in the present disclosure and claims, the terms "parasiticidal" and "parasiticidally" refers to observable effects on a parasitic nematode to provide protection of a plant, animal or human from the nematode. Parasiticidal effects typically relate to diminishing the occurrence or activity of the target parasitic nematode. Such effects on the nematode include necrosis, death, retarded growth, diminished mobility or lessened ability to remain on or in the host plant, animal or human, reduced feeding and inhibition of reproduction. These effects on parasitic nematodes provide control (including prevention, reduction or elimination) of parasitic infestation or infection of the plant, animal or human. Therefore "control" of a parasitic nematode means achieving a parasiticidal effect on the nematode. The expressions "parasiticidally effective amount" and "biologically effective amount" in the context of applying a chemical compound to control a parasitic nematode refer an amount of the compound that is sufficient to control the parasitic nematode.

The term "agronomic" refers to the production of field crops such as for food and fiber and includes the growth of soybeans and other legumes, cereal (e.g., wheat, oats, barley, rye, rice, maize/corn), leafy vegetables (e.g., lettuce, cabbage, and other cole crops), fruiting vegetables (e.g., tomatoes, pepper, eggplant, crucifers and cucurbits), potatoes, sweet potatoes, grapes, cotton, tree fruits (e.g., pome, stone and citrus), small fruit (berries, cherries) and other specialty crops (e.g., canola, sunflower, olives).

The term "nonagronomic" refers to other than field crops, such as horticultural crops (e.g., greenhouse, nursery or ornamental plants not grown in a field), residential, agricultural, commercial and industrial structures, turf (e.g., sod farm, pasture, golf course, lawn, sports field, etc.), wood products, stored product, agro-forestry and vegetation management, public health (i.e. human) and animal health (e.g., domesticated animals such as pets, livestock and poultry, undomesticated animals such as wildlife) applications.

Nonagronomic applications include protecting an animal from a parasitic nematode by administering a parasiticidally effective (i.e. biologically effective) amount of a compound of the invention, typically in the form of a composition formulated for veterinary use, to the animal to be protected.

In the above recitations, the term "alkyl", used either alone or in compound words such as "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl.

"Alkoxy" includes, for example, methoxy, ethoxy, n-propyloxy, isopropyloxy and the different butoxy, pentoxy and hexyloxy isomers.

"Cycloalkyl" includes, for example, cyclopropyl, cyclobutyl, cyclopentyl and cyclohexyl. The term "cycloalkylalkyl" denotes cycloalkyl substitution on an alkyl moiety. Examples of "cycloalkylalkyl" include cyclopropylmethyl, cyclopentylethyl, and other cycloalkyl moieties bonded to straight-chain or branched alkyl groups.

The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include $F_3C$, $ClCH_2$, $CF_3CH_2$ and $CF_3CCl_2$.

The term "alkylthio" includes straight-chain or branched alkylthio moieties such as methylthio, ethylthio, and the different propylthio, butylthio, pentylthio and hexylthio isomers. "Alkylsulfinyl" includes both enantiomers of an alkylsulfinyl group. Examples of "alkylsulfinyl" include $CH_3S(=O)$, $CH_3CH_2S(=O)$, $CH_3CH_2CH_2S(=O)$, $(CH_3)_2CHS(=O)$ and the different butylsulfinyl, pentylsulfinyl and hexylsulfinyl isomers. Examples of "alkylsulfonyl" include $CH_3S(=O)_2$, $CH_3CH_2S(=O)_2$, $CH_3CH_2CH_2S(=O)_2$, $(CH_3)_2CHS(=O)_2$, and the different butylsulfonyl, pentylsulfonyl and hexylsulfonyl isomers. The chemical abbreviations $S(O)$ and $S(=O)$ as used herein represent a sulfinyl moiety. The chemical abbreviations $SO_2$, $S(O)_2$ and $S(=O)_2$ as used herein represent a sulfonyl moiety.

"Alkylcarbonyl" denotes a straight-chain or branched alkyl moiety bonded to a $C(O)$ moiety. The chemical abbreviations $C(O)$ and $C(=O)$ as used herein represent a carbonyl moiety. Examples of "alkylcarbonyl" include $C(O)CH_3$, $C(O)CH_2CH_2CH_3$ and $C(O)CH(CH_3)_2$.

"Alkoxycarbonyl" denotes a straight-chain or branched alkyl moiety bonded to a $CO_2$ moiety. The chemical abbreviations $CO_2$, $C(O)O$ and $C(=O)O$ as used herein represent an oxycarbonyl moiety. Examples of "alkoxycarbonyl" include $C(O)OCH_3$, $C(O)OCH_2CH_3$, $C(O)OCH_2CH_2CH_3$ and $C(O)OCH(CH_3)_2$.

The total number of carbon atoms in a substituent group is indicated by the "$C_i$-$C_j$" prefix. For example, $C_1$-$C_6$ alkyl designates methyl, ethyl, and the various propyl, butyl, pentyl and hexyl isomers.

As used herein, the following definitions shall apply unless otherwise indicated. The term "optionally substituted" is used interchangeably with the phrase "substituted or unsubstituted" or with the term "(un)substituted". The expression "optionally substituted with 1 to 4 substituents" means that no substituent is present (i.e. unsubstituted) or that 1, 2, 3 or 4 substituents are present (limited by the number of available bonding positions). Unless otherwise indicated, an optionally substituted group may have a substituent at each substitutable position of the group, and each substitution is independent of the other.

A wide variety of synthetic methods are known in the art to enable preparation of aromatic and nonaromatic heterocyclic rings and ring systems; for extensive reviews see the eight volume set of *Comprehensive Heterocyclic Chemistry*, A. R. Katritzky and C. W. Rees editors-in-chief, Pergamon Press, Oxford, 1984 and the twelve volume set of *Comprehensive Heterocyclic Chemistry II*, A. R. Katritzky, C. W. Rees and E. F. V. Scriven editors-in-chief, Pergamon Press, Oxford, 1996.

Compounds selected from Formula 1, 1a or 1b, may exist in more than one form, and Formula 1, 1a or 1b thus includes all crystalline and non-crystalline forms of the compounds that Formula 1, 1a or 1b represents. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound represented by Formula 1, 1a or 1b can exhibit beneficial effects (e.g., suitability for preparation of useful formulations, improved biological performance) relative to another polymorph or a mixture of polymorphs of the same compound represented by Formula 1, 1a or 1b. Preparation and isolation of a particular polymorph of a compound represented by Formula 1, 1a or 1b can be achieved by methods known to those skilled in the art including, for example, crystallization using selected solvents and temperatures.

Embodiments of the present invention as described in the Summary of the Invention include those described below. In the following Embodiments, reference to a compound of Formula 1, 1a or 1b includes the definitions of substituents specified in the Summary of the Invention unless further defined in the Embodiments.

Embodiment 1. A compound of Formula 1a.

Embodiment 2. A compound of Formula 1b.

Embodiment 3. A compound of Formula 1, 1a or 1b wherein $R^2$ is H.

Embodiment 4. A compound of Formula 1, 1a or 1b wherein $R^3$ is $C_2$-$C_6$ alkyl or $C_3$-$C_6$ cycloalkyl, each unsubstituted or substituted with at least one $R^6$.

Embodiment 4a. A compound of Formula 1, 1a or 1b wherein $R^3$ is $C_2$-$C_6$ alkyl or $C_3$-$C_6$ cycloalkyl.

Embodiment 4b. A compound of Formula 1, 1a or 1b wherein $R^3$ is $C_3$-$C_6$ alkyl or cyclopropyl.

Embodiment 4c. A compound of Formula 1, 1a or 1b wherein $R^3$ is isopropyl, s-butyl, t-butyl, $CH_2C(CH_3)_3$ or cyclopropyl.

Embodiment 4d. A compound of Formula 1, 1a or 1b wherein $R^3$ is t-butyl or cyclopropyl.

Embodiment 4e. A compound of Formula 1, 1a or 1b wherein $R^3$ is isopropyl.

Embodiment 4f. A compound of Formula 1, 1a or 1b wherein $R^3$ is s-butyl.

Embodiment 4g. A compound of Formula 1, 1a or 1b wherein $R^3$ is t-butyl.

Embodiment 4h. A compound of Formula 1, 1a or 1b wherein $R^3$ is $CH_2C(CH_3)_3$.

Embodiment 4i. A compound of Formula 1, 1a or 1b wherein $R^3$ is cyclopropyl.
Embodiment 5. A compound of Formula 1 wherein $R^3$ is isopropyl.
Embodiment 5a. A compound of Formula 1 wherein $R^3$ is s-butyl.
Embodiment 5b. A compound of Formula 1 wherein $R^3$ is t-butyl.
Embodiment 5c. A compound of Formula 1 wherein $R^3$ is $CH_2C(CH_3)_3$.
Embodiment 5d. A compound of Formula 1 wherein $R^3$ is cyclopropyl.
Embodiment 6. A compound of Formula 1a wherein $R^3$ is isopropyl.
Embodiment 6a. A compound of Formula 1a wherein $R^3$ is s-butyl.
Embodiment 6b. A compound of Formula 1a wherein $R^3$ is t-butyl.
Embodiment 6c. A compound of Formula 1a wherein $R^3$ is $CH_2C(CH_3)_3$.
Embodiment 6d. A compound of Formula 1a wherein $R^3$ is cyclopropyl.
Embodiment 7. A compound of Formula 1b wherein $R^3$ is isopropyl.
Embodiment 7a. A compound of Formula 1b wherein $R^3$ is s-butyl.
Embodiment 7b. A compound of Formula 1b wherein $R^3$ is t-butyl.
Embodiment 7c. A compound of Formula 1b wherein $R^3$ is $CH_2C(CH_3)_3$.
Embodiment 7d. A compound of Formula 1b wherein $R^3$ is cyclopropyl.
Embodiment 8. A compound of Formula 1, 1a or 1b wherein $R^4$ is Cl or Br.
Embodiment 8a. A compound of Formula 1, 1a or 1b wherein $R^4$ is Cl.
Embodiment 8b. A compound of Formula 1, 1a or 1b wherein $R^4$ is Br.
Embodiment 9. A compound of Formula 1 wherein $R^4$ is Cl or Br.
Embodiment 9a. A compound of Formula 1 wherein $R^4$ is Cl.
Embodiment 9b. A compound of Formula 1 wherein $R^4$ is Br.
Embodiment 10. A compound of Formula 1a wherein $R^4$ is Cl or Br.
Embodiment 10a. A compound of Formula 1a wherein $R^4$ is Cl.
Embodiment 10b. A compound of Formula 1a wherein $R^4$ is Br.
Embodiment 11. A compound of Formula 1b wherein $R^4$ is Cl or Br.
Embodiment 11a. A compound of Formula 1b wherein $R^4$ is Cl.
Embodiment 11b. A compound of Formula 1b wherein $R^4$ is Br.

Embodiments of this invention, including Embodiments 1-11b above as well as any other embodiments described herein, can be combined in any manner, and the descriptions of variables in the embodiments pertain not only to the compounds of Formula 1, 1a or 1b but also to the starting compounds and intermediate compounds useful for preparing the compounds of Formula 1, 1a or 1b. In addition, embodiments of this invention, including Embodiments 1-11b above as well as any other embodiments described herein, and any combination thereof, pertain to the compositions and methods of the present invention.

Combinations of Embodiments 1-11b are illustrated by:

Embodiment A

A compound of Formula 1a wherein
$R^2$ is H;
$R^3$ is $C_2$-$C_6$ alkyl or $C_3$-$C_6$ cycloalkyl, each unsubstituted or substituted with at least one $R^6$;
$R^4$ is Cl, Br, I, $CH_3$, $CF_3$ or cyano;
each $R^6$ is independently halogen, cyano, $C_1$-$C_3$ alkoxy, $C_3$-$C_6$ cycloalkyl, $C_1$-$C_3$ alkylthio, $C_1$-$C_3$ alkylsulfinyl, $C_1$-$C_3$ alkylsulfonyl or $SiR^aR^bR^c$; and
each $R^a$, $R^b$ and $R^c$ is independently $C_1$-$C_6$ alkyl.

Embodiment B

A compound of Formula 1a wherein
$R^2$ is H;
$R^3$ is $C_2$-$C_6$ alkyl or $C_3$-$C_6$ cycloalkyl; and
$R^4$ is Cl or Br.

Embodiment C

A compound of Formula 1a wherein
$R^2$ is H;
$R^3$ is $C_3$-$C_6$ alkyl or cyclopropyl; and
$R^4$ is Cl or Br.

Embodiment D

A compound of Formula 1a wherein
$R^2$ is H;
$R^3$ is t-butyl or cyclopropyl; and
$R^4$ is Cl or Br.

Embodiment E

A compound of Formula 1a wherein
$R^2$ is H;
$R^3$ is isopropyl, s-butyl, t-butyl, $CH_2C(CH_3)_3$ or cyclopropyl; and
$R^4$ is Cl or Br.

Embodiment E1

A compound of Formula 1a wherein
$R^2$ is H;
$R^3$ is isopropyl, s-butyl, t-butyl, $CH_2C(CH_3)_3$ or cyclopropyl; and
$R^4$ is Cl.

Embodiment E2

A compound of Formula 1a wherein
$R^2$ is H;
$R^3$ is isopropyl, s-butyl, t-butyl, $CH_2C(CH_3)_3$ or cyclopropyl; and
$R^4$ is Br.

Embodiment F1

A compound of Formula 1a wherein
$R^2$ is H;
$R^3$ is isopropyl; and
$R^4$ is Cl.

Embodiment F2

A compound of Formula 1a wherein
$R^2$ is H;
$R^3$ is s-butyl; and
$R^4$ is Cl.

Embodiment F3

A compound of Formula 1a wherein
$R^2$ is H;
$R^3$ is t-butyl; and
$R^4$ is Cl.

Embodiment F4

A compound of Formula 1a wherein
$R^2$ is H;
$R^3$ is $CH_2C(CH_3)_3$; and
$R^4$ is Cl.

Embodiment F5

A compound of Formula 1a wherein
$R^2$ is H;
$R^3$ is cyclopropyl; and
$R^4$ is Cl.

Embodiment G1

A compound of Formula 1a wherein
$R^2$ is H;
$R^3$ is isopropyl; and
$R^4$ is Br.

Embodiment G2

A compound of Formula 1a wherein
$R^2$ is H;
$R^3$ is s-butyl; and
$R^4$ is Br.

Embodiment G3

A compound of Formula 1a wherein
$R^2$ is H;
$R^3$ is t-butyl; and
$R^4$ is Br.

Embodiment G4

A compound of Formula 1a wherein
$R^2$ is H;
$R^3$ is $CH_2C(CH_3)_3$; and
$R^4$ is Br.

Embodiment G5

A compound of Formula 1a wherein
$R^2$ is H;
$R^3$ is cyclopropyl; and
$R^4$ is Br.

Embodiment H

A compound of Formula 1b wherein
$R^2$ is H;
$R^3$ is $C_2$-$C_6$ alkyl or $C_3$-$C_6$ cycloalkyl, each unsubstituted or substituted with at least one $R^6$;
$R^4$ is Cl, Br, I, $CH_3$, $CF_3$ or cyano;
each $R^6$ is independently halogen, cyano, $C_1$-$C_3$ alkoxy, $C_3$-$C_6$ cycloalkyl, $C_1$-$C_3$ alkylthio, $C_1$-$C_3$ alkylsulfinyl, $C_1$-$C_3$ alkylsulfonyl or $SiR^aR^bR^c$; and
each $R^a$, $R^b$ and $R^c$ is independently $C_1$-$C_6$ alkyl.

Embodiment I

A compound of Formula 1b wherein
$R^2$ is H;
$R^3$ is $C_2$-$C_6$ alkyl or $C_3$-$C_6$ cycloalkyl; and
$R^4$ is Cl or Br.

Embodiment J

A compound of Formula 1b wherein
$R^2$ is H;
$R^3$ is $C_3$-$C_6$ alkyl or cyclopropyl; and
$R^4$ is Cl or Br.

Embodiment K

A compound of Formula 1b wherein
$R^2$ is H;
$R^3$ is t-butyl or cyclopropyl; and
$R^4$ is Cl or Br.

Embodiment L

A compound of Formula 1b wherein
$R^2$ is H;
$R^3$ is isopropyl, s-butyl, t-butyl, $CH_2C(CH_3)_3$ or cyclopropyl; and
$R^4$ is Cl or Br.

Embodiment M1

A compound of Formula 1b wherein
$R^2$ is H;
$R^3$ is isopropyl, s-butyl, t-butyl, $CH_2C(CH_3)_3$ or cyclopropyl; and
$R^4$ is Cl.

Embodiment M2

A compound of Formula 1b wherein
$R^2$ is H;
$R^3$ is isopropyl, s-butyl, t-butyl, $CH_2C(CH_3)_3$ or cyclopropyl; and
$R^4$ is Br.

Embodiment N1

A compound of Formula 1b wherein
$R^2$ is H;
$R^3$ is isopropyl; and
$R^4$ is Cl.

Embodiment N2

A compound of Formula 1b wherein
$R^2$ is H;
$R^3$ is s-butyl; and
$R^4$ is Cl.

Embodiment N3

A compound of Formula 1b wherein
$R^2$ is H;
$R^3$ is t-butyl; and
$R^4$ is Cl.

Embodiment N4

A compound of Formula 1b wherein
$R^2$ is H;
$R^3$ is $CH_2C(CH_3)_3$; and
$R^4$ is Cl.

Embodiment N5

A compound of Formula 1b wherein
$R^2$ is H;
$R^3$ is cyclopropyl; and
$R^4$ is Cl.

Embodiment O1

A compound of Formula 1b wherein
$R^2$ is H;
$R^3$ is isopropyl; and
$R^4$ is Br.

Embodiment O2

A compound of Formula 1b wherein
$R^2$ is H;
$R^3$ is s-butyl; and
$R^4$ is Br.

Embodiment O3

A compound of Formula 1b wherein
$R^2$ is H;
$R^3$ is t-butyl; and
$R^4$ is Br.

Embodiment O4

A compound of Formula 1b wherein
$R^2$ is H;
$R^3$ is $CH_2C(CH_3)_3$; and
$R^4$ is Br.

Embodiment O5

A compound of Formula 1b wherein
$R^2$ is H;
$R^3$ is cyclopropyl; and
$R^4$ is Br.

Embodiment P1

A compound of Formula 1 wherein
$R^2$ is H;
$R^3$ is $-CR^{6a}R^{6b}R^{6c}$;
$R^4$ is Cl or Br;
$R^{6a}$ is H, $C_1$-$C_3$ alkyl, $C_2$-$C_3$ alkenyl or $C_3$-$C_6$ cycloalkyl;
$R^{6b}$ is $C_1$-$C_3$ alkyl;
$R^{6c}$ is H, halogen, cyano, $C_1$-$C_3$ alkoxy, $C_1$-$C_3$ alkylthio, $C_1$-$C_3$ alkylsulfinyl, $C_1$-$C_3$ alkylsulfonyl or $-CR^{7a}R^{7b}R^{7c}$;
$R^{7a}$ is H, halogen, cyano, $C_1$-$C_3$ alkoxy, $C_1$-$C_3$ alkylthio, $C_1$-$C_3$ alkylsulfinyl, $C_1$-$C_3$ alkylsulfonyl or $C_1$-$C_2$ alkyl;
$R^{7b}$ is H, halogen, cyano or $C_1$-$C_2$ alkyl; and
$R^{7c}$ is H, halogen, cyano or $C_1$-$C_2$ alkyl.

Embodiment P2

A compound of Formula 1a wherein
$R^2$ is H;
$R^3$ is $-CR^{6a}R^{6b}R^{6c}$;
$R^4$ is Cl or Br;
$R^{6a}$ is H, $C_1$-$C_3$ alkyl, $C_2$-$C_3$ alkenyl or $C_3$-$C_6$ cycloalkyl;
$R^{6b}$ is $C_1$-$C_3$ alkyl;
$R^{6c}$ is H, halogen, cyano, $C_1$-$C_3$ alkoxy, $C_1$-$C_3$ alkylthio, $C_1$-$C_3$ alkylsulfinyl, $C_1$-$C_3$ alkylsulfonyl or $-CR^{7a}R^{7b}R^{7c}$;
$R^{7a}$ is H, halogen, cyano, $C_1$-$C_3$ alkoxy, $C_1$-$C_3$ alkylthio, $C_1$-$C_3$ alkylsulfinyl, $C_1$-$C_3$ alkylsulfonyl or $C_1$-$C_2$ alkyl;
$R^{7b}$ is H, halogen, cyano or $C_1$-$C_2$ alkyl; and
$R^{7c}$ is H, halogen, cyano or $C_1$-$C_2$ alkyl.

Embodiment P3

A compound of Formula 1b wherein
$R^2$ is H;
$R^3$ is $-CR^{6a}R^{6b}R^{6c}$;
$R^4$ is Cl or Br;
$R^{6a}$ is H, $C_1$-$C_3$ alkyl, $C_2$-$C_3$ alkenyl or $C_3$-$C_6$ cycloalkyl;
$R^{6b}$ is $C_1$-$C_3$ alkyl;
$R^{6c}$ is H, halogen, cyano, $C_1$-$C_3$ alkoxy, $C_1$-$C_3$ alkylthio, $C_1$-$C_3$ alkylsulfinyl, $C_1$-$C_3$ alkylsulfonyl or $-CR^{7a}R^{7b}R^{7c}$;
$R^{7a}$ is H, halogen, cyano, $C_1$-$C_3$ alkoxy, $C_1$-$C_3$ alkylthio, $C_1$-$C_3$ alkylsulfinyl, $C_1$-$C_3$ alkylsulfonyl or $C_1$-$C_2$ alkyl;
$R^{7b}$ is H, halogen, cyano or $C_1$-$C_2$ alkyl; and
$R^{7c}$ is H, halogen, cyano or $C_1$-$C_2$ alkyl.

Embodiment Q1

A composition comprising (i) a compound of Formula 1a and a compound of Formula 1b, wherein the ratio of 1b to 1a is at least 55:45; and
wherein $R^2$ is H; or $C_1$-$C_6$ alkyl, $C_2$-$C_6$ alkenyl, $C_2$-$C_6$ alkynyl, $C_3$-$C_6$ cycloalkyl, $C_2$-$C_6$ alkylcarbonyl, $C_2$-$C_6$ alkoxycarbonyl, $C_1$-$C_6$ alkylthio or $C_1$-$C_6$ alkylsulfonyl, each unsubstituted or substituted with at least one $R^5$;

$R^3$ is $C_2$-$C_{16}$ alkyl, $C_2$-$C_{16}$ alkenyl, $C_2$-$C_{16}$ alkynyl or $C_3$-$C_6$ cycloalkyl, each unsubstituted or substituted with at least one $R^6$;

$R^4$ is Cl, Br, I, $CH_3$, $CF_3$ or cyano;

each $R^5$ is independently halogen, cyano, $C_1$-$C_3$ alkoxy, $C_3$-$C_6$ cycloalkyl, $C_1$-$C_3$ alkylthio, $C_1$-$C_3$ alkylsulfinyl or $C_1$-$C_3$ alkylsulfonyl;

each $R^6$ is independently halogen, cyano, $C_1$-$C_3$ alkoxy, $C_3$-$C_6$ cycloalkyl, $C_1$-$C_3$ alkylthio, $C_1$-$C_3$ alkylsulfinyl, $C_1$-$C_3$ alkylsulfonyl or $SiR^aR^bR^c$; and each $R^a$, $R^b$ and $R^c$ is independently $C_1$-$C_6$ alkyl; and (ii) at least one additional component selected from the group consisting of surfactants, solid diluents and liquid diluents.

Embodiment Q2

A composition comprising (i) a compound of Formula 1a and a compound of Formula 1b, wherein the ratio of 1b to 1a is at least 65:35; and wherein $R^2$ is H; or $C_1$-$C_6$ alkyl, $C_2$-$C_6$ alkenyl, $C_2$-$C_6$ alkynyl, $C_3$-$C_6$ cycloalkyl, $C_2$-$C_6$ alkylcarbonyl, $C_2$-$C_6$ alkoxycarbonyl, $C_1$-$C_6$ alkylthio or $C_1$-$C_6$ alkylsulfonyl, each unsubstituted or substituted with at least one $R^5$;

$R^3$ is $C_2$-$C_{16}$ alkyl, $C_2$-$C_{16}$ alkenyl, $C_2$-$C_{16}$ alkynyl or $C_3$-$C_6$ cycloalkyl, each unsubstituted or substituted with at least one $R^6$;

$R^4$ is Cl, Br, I, $CH_3$, $CF_3$ or cyano;

each $R^5$ is independently halogen, cyano, $C_1$-$C_3$ alkoxy, $C_3$-$C_6$ cycloalkyl, $C_1$-$C_3$ alkylthio, $C_1$-$C_3$ alkylsulfinyl or $C_1$-$C_3$ alkylsulfonyl;

each $R^6$ is independently halogen, cyano, $C_1$-$C_3$ alkoxy, $C_3$-$C_6$ cycloalkyl, $C_1$-$C_3$ alkylthio, $C_1$-$C_3$ alkylsulfinyl, $C_1$-$C_3$ alkylsulfonyl or $SiR^aR^bR^c$; and each $R^a$, $R^b$ and $R^c$ is independently $C_1$-$C_6$ alkyl; and (ii) at least one additional component selected from the group consisting of surfactants, solid diluents and liquid diluents.

Embodiment Q3

A composition comprising (i) a compound of Formula 1a and a compound of Formula 1b, wherein the ratio of 1b to 1a is at least 75:25; and wherein $R^2$ is H; or $C_1$-$C_6$ alkyl, $C_2$-$C_6$ alkenyl, $C_2$-$C_6$ alkynyl, $C_3$-$C_6$ cycloalkyl, $C_2$-$C_6$ alkylcarbonyl, $C_2$-$C_6$ alkoxycarbonyl, $C_1$-$C_6$ alkylthio or $C_1$-$C_6$ alkylsulfonyl, each unsubstituted or substituted with at least one $R^5$;

$R^3$ is $C_2$-$C_{16}$ alkyl, $C_2$-$C_{16}$ alkenyl, $C_2$-$C_{16}$ alkynyl or $C_3$-$C_6$ cycloalkyl, each unsubstituted or substituted with at least one $R^6$;

$R^4$ is Cl, Br, I, $CH_3$, $CF_3$ or cyano;

each $R^5$ is independently halogen, cyano, $C_1$-$C_3$ alkoxy, $C_3$-$C_6$ cycloalkyl, $C_1$-$C_3$ alkylthio, $C_1$-$C_3$ alkylsulfinyl or $C_1$-$C_3$ alkylsulfonyl;

each $R^6$ is independently halogen, cyano, $C_1$-$C_3$ alkoxy, $C_3$-$C_6$ cycloalkyl, $C_1$-$C_3$ alkylthio, $C_1$-$C_3$ alkylsulfinyl, $C_1$-$C_3$ alkylsulfonyl or $SiR^aR^bR^c$; and each $R^a$, $R^b$ and $R^c$ is independently $C_1$-$C_6$ alkyl; and (ii) at least one additional component selected from the group consisting of surfactants, solid diluents and liquid diluents.

Embodiment Q4

A composition comprising (i) a compound of Formula 1a and a compound of Formula 1b, wherein the ratio of 1b to 1a is at least 85:15; and wherein $R^2$ is H; or $C_1$-$C_6$ alkyl, $C_2$-$C_6$ alkenyl, $C_2$-$C_6$ alkynyl, $C_3$-$C_6$ cycloalkyl, $C_2$-$C_6$ alkylcarbonyl, $C_2$-$C_6$ alkoxycarbonyl, $C_1$-$C_6$ alkylthio or $C_1$-$C_6$ alkylsulfonyl, each unsubstituted or substituted with at least one $R^5$;

$R^3$ is $C_2$-$C_{16}$ alkyl, $C_2$-$C_{16}$ alkenyl, $C_2$-$C_{16}$ alkynyl or $C_3$-$C_6$ cycloalkyl, each unsubstituted or substituted with at least one $R^6$;

$R^4$ is Cl, Br, I, $CH_3$, $CF_3$ or cyano;

each $R^5$ is independently halogen, cyano, $C_1$-$C_3$ alkoxy, $C_3$-$C_6$ cycloalkyl, $C_1$-$C_3$ alkylthio, $C_1$-$C_3$ alkylsulfinyl or $C_1$-$C_3$ alkylsulfonyl;

each $R^6$ is independently halogen, cyano, $C_1$-$C_3$ alkoxy, $C_3$-$C_6$ cycloalkyl, $C_1$-$C_3$ alkylthio, $C_1$-$C_3$ alkylsulfinyl, $C_1$-$C_3$ alkylsulfonyl or $SiR^aR^bR^c$; and each $R^a$, $R^b$ and $R^c$ is independently $C_1$-$C_6$ alkyl; and (ii) at least one additional component selected from the group consisting of surfactants, solid diluents and liquid diluents.

Embodiment Q5

A composition comprising (i) a compound of Formula 1a and a compound of Formula 1b, wherein the ratio of 1b to 1a is at least 95:5; and wherein $R^2$ is H; or $C_1$-$C_6$ alkyl, $C_2$-$C_6$ alkenyl, $C_2$-$C_6$ alkynyl, $C_3$-$C_6$ cycloalkyl, $C_2$-$C_6$ alkylcarbonyl, $C_2$-$C_6$ alkoxycarbonyl, $C_1$-$C_6$ alkylthio or $C_1$-$C_6$ alkylsulfonyl, each unsubstituted or substituted with at least one $R^5$;

$R^3$ is $C_2$-$C_{16}$ alkyl, $C_2$-$C_{16}$ alkenyl, $C_2$-$C_{16}$ alkynyl or $C_3$-$C_6$ cycloalkyl, each unsubstituted or substituted with at least one $R^6$;

$R^4$ is Cl, Br, I, $CH_3$, $CF_3$ or cyano;

each $R^5$ is independently halogen, cyano, $C_1$-$C_3$ alkoxy, $C_3$-$C_6$ cycloalkyl, $C_1$-$C_3$ alkylthio, $C_1$-$C_3$ alkylsulfinyl or $C_1$-$C_3$ alkylsulfonyl;

each $R^6$ is independently halogen, cyano, $C_1$-$C_3$ alkoxy, $C_3$-$C_6$ cycloalkyl, $C_1$-$C_3$ alkylthio, $C_1$-$C_3$ alkylsulfinyl, $C_1$-$C_3$ alkylsulfonyl or $SiR^aR^bR^c$; and each $R^a$, $R^b$ and $R^c$ is independently $C_1$-$C_6$ alkyl; and (ii) at least one additional component selected from the group consisting of surfactants, solid diluents and liquid diluents.

Embodiment Q6

A composition comprising (i) a compound of Formula 1a and a compound of Formula 1b, wherein the ratio of 1b to 1a is at least 97:3; and wherein $R^2$ is H; or $C_1$-$C_6$ alkyl, $C_2$-$C_6$ alkenyl, $C_2$-$C_6$ alkynyl, $C_3$-$C_6$ cycloalkyl, $C_2$-$C_6$ alkylcarbonyl, $C_2$-$C_6$ alkoxycarbonyl, $C_1$-$C_6$ alkylthio or $C_1$-$C_6$ alkylsulfonyl, each unsubstituted or substituted with at least one $R^5$;

$R^3$ is $C_2$-$C_{16}$ alkyl, $C_2$-$C_{16}$ alkenyl, $C_2$-$C_{16}$ alkynyl or $C_3$-$C_6$ cycloalkyl, each unsubstituted or substituted with at least one $R^6$;

$R^4$ is Cl, Br, I, $CH_3$, $CF_3$ or cyano;

each $R^5$ is independently halogen, cyano, $C_1$-$C_3$ alkoxy, $C_3$-$C_6$ cycloalkyl, $C_1$-$C_3$ alkylthio, $C_1$-$C_3$ alkylsulfinyl or $C_1$-$C_3$ alkylsulfonyl;

each $R^6$ is independently halogen, cyano, $C_1$-$C_3$ alkoxy, $C_3$-$C_6$ cycloalkyl, $C_1$-$C_3$ alkylthio, $C_1$-$C_3$ alkylsulfinyl, $C_1$-$C_3$ alkylsulfonyl or $SiR^aR^bR^c$; and each $R^a$, $R^b$ and $R^c$ is independently $C_1$-$C_6$ alkyl; and (ii) at least one additional component selected from the group consisting of surfactants, solid diluents and liquid diluents.

Embodiment Q7

A composition comprising (i) a compound of Formula 1a and a compound of Formula 1b, wherein the ratio of 1b to 1a is at least 99:1; and wherein $R^2$ is H; or $C_1$-$C_6$ alkyl, $C_2$-$C_6$ alkenyl, $C_2$-$C_6$ alkynyl, $C_3$-$C_6$ cycloalkyl, $C_2$-$C_6$ alkylcarbonyl, $C_2$-$C_6$ alkoxycarbonyl, $C_1$-$C_6$ alkylthio or $C_1$-$C_6$ alkylsulfonyl, each unsubstituted or substituted with at least one $R^5$;

$R^3$ is $C_2$-$C_{16}$ alkyl, $C_2$-$C_{16}$ alkenyl, $C_2$-$C_{16}$ alkynyl or $C_3$-$C_6$ cycloalkyl, each unsubstituted or substituted with at least one $R^6$;

$R^4$ is Cl, Br, I, $CH_3$, $CF_3$ or cyano;

each $R^5$ is independently halogen, cyano, $C_1$-$C_3$ alkoxy, $C_3$-$C_6$ cycloalkyl, $C_1$-$C_3$ alkylthio, $C_1$-$C_3$ alkylsulfinyl or $C_1$-$C_3$ alkylsulfonyl;

each $R^6$ is independently halogen, cyano, $C_1$-$C_3$ alkoxy, $C_3$-$C_6$ cycloalkyl, $C_1$-$C_3$ alkylthio, $C_1$-$C_3$ alkylsulfinyl, $C_1$-$C_3$ alkylsulfonyl or $SiR^aR^bR^c$; and each $R^a$, $R^b$ and $R^c$ is independently $C_1$-$C_6$ alkyl; and (ii) at least one additional component selected from the group consisting of surfactants, solid diluents and liquid diluents.

Embodiment Q8

A composition comprising (i) a compound of Formula 1a and a compound of Formula 1b, wherein the ratio of 1b to 1a is essentially 100:0; and wherein $R^2$ is H; or $C_1$-$C_6$ alkyl, $C_2$-$C_6$ alkenyl, $C_2$-$C_6$ alkynyl, $C_3$-$C_6$ cycloalkyl, $C_2$-$C_6$ alkylcarbonyl, $C_2$-$C_6$ alkoxycarbonyl, $C_1$-$C_6$ alkylthio or $C_1$-$C_6$ alkylsulfonyl, each unsubstituted or substituted with at least one $R^5$;

$R^3$ is $C_2$-$C_{16}$ alkyl, $C_2$-$C_{16}$ alkenyl, $C_2$-$C_{16}$ alkynyl or $C_3$-$C_6$ cycloalkyl, each unsubstituted or substituted with at least one $R^6$;

$R^4$ is Cl, Br, I, $CH_3$, $CF_3$ or cyano;

each $R^5$ is independently halogen, cyano, $C_1$-$C_3$ alkoxy, $C_3$-$C_6$ cycloalkyl, $C_1$-$C_3$ alkylthio, $C_1$-$C_3$ alkylsulfinyl or $C_1$-$C_3$ alkylsulfonyl;

each $R^6$ is independently halogen, cyano, $C_1$-$C_3$ alkoxy, $C_3$-$C_6$ cycloalkyl, $C_1$-$C_3$ alkylthio, $C_1$-$C_3$ alkylsulfinyl, $C_1$-$C_3$ alkylsulfonyl or $SiR^aR^bR^c$; and each $R^a$, $R^b$ and $R^c$ is independently $C_1$-$C_6$ alkyl; and (ii) at least one additional component selected from the group consisting of surfactants, solid diluents and liquid diluents.

Embodiment R1

A method for controlling a soil-dwelling nematode comprising contacting the nematode or its environment with a biologically effective amount of a compound selected from Formula 2,

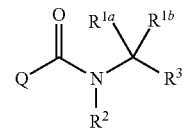

wherein

Q is a furan, thiophene or thiazole ring substituted with $R^4$ at a carbon atom adjacent to the carbon atom through which the furan, thiophene or thiazole ring is bonded to the remainder of Formula 2;

$R^{1a}$ is $C_1$-$C_6$ alkyl or $C_3$-$C_6$ cycloalkyl, each unsubstituted or substituted with at least one $R^5$;

$R^{1b}$ is H or $C_1$-$C_3$ alkyl; or $R^{1a}$ and $R^{1b}$ are taken together with the carbon atom to which they are attached to form a 3- to 6-membered cycloalkyl ring, unsubstituted or substituted with at least one $R^5$;

$R^2$ is H; or $C_1$-$C_6$ alkyl, $C_2$-$C_6$ alkenyl, $C_2$-$C_6$ alkynyl, $C_3$-$C_6$ cycloalkyl, $C_2$-$C_6$ alkylcarbonyl, $C_2$-$C_6$ alkoxycarbonyl, $C_1$-$C_6$ alkylthio or $C_1$-$C_6$ alkylsulfonyl, each unsubstituted or substituted with at least one $R^5$;

$R^3$ is $C_2$-$C_{16}$ alkyl, $C_2$-$C_{16}$ alkenyl, $C_2$-$C_{16}$ alkynyl or $C_3$-$C_6$ cycloalkyl, each unsubstituted or substituted with at least one $R^6$;

$R^4$ is Cl, Br, I, $CH_3$, $CF_3$ or cyano; provided that when $R^4$ is Me, then $R^3$ is other than unsubstituted $C_2$ alkyl;

each $R^5$ is independently halogen, cyano, $C_1$-$C_3$ alkoxy, $C_3$-$C_6$ cycloalkyl, $C_1$-$C_3$ alkylthio, $C_1$-$C_3$ alkylsulfinyl, or $C_1$-$C_3$ alkylsulfonyl;

each $R^6$ is independently halogen, cyano, $C_1$-$C_3$ alkoxy, $C_3$-$C_6$ cycloalkyl, $C_1$-$C_3$ alkylthio, $C_1$-$C_3$ alkylsulfinyl, $C_1$-$C_3$ alkylsulfonyl or $SiR^aR^bR^c$; and each $R^a$, $R^b$ and $R^c$ is independently $C_1$-$C_6$ alkyl.

Embodiment R2

The method of Embodiment R1 wherein Q is selected from the group consisting of:

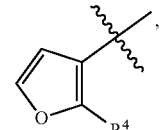

Q-1

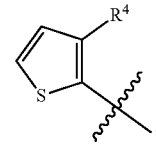

Q-2

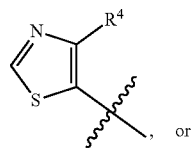

Q-3, or

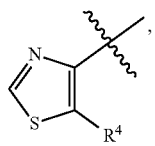

Q-4

Embodiment R3

The method of Embodiment R1 wherein Q is Q-1.

Specific embodiments include compounds of Formula 1 and 1b selected from the group consisting of (compound numbers refer to Index Tables A-C2):
compound 9;
compound 11;
compound 26;
compound 40;
compound 43;
compound 78;
compound 80; and
compound 84.

Specific embodiments further include compounds of Formula 1b selected from the group consisting of (compound numbers refer to Index Tables A-C2):
compound 9;
compound 11;
compound 26;
compound 40;
compound 43;
compound 78;
compound 80; and
compound 84.

Of note is that compounds of this invention are characterized by favorable metabolic and/or soil residual patterns and exhibit activity controlling a spectrum of agronomic and nonagronomic parasitic nematodes.

Of particular note, for reasons of parasitic nematode control spectrum and economic importance, protection of agronomic crops from damage or injury caused by parasitic nematodes by controlling parasitic nematodes are embodiments of the invention. Compounds of this invention because of their favorable translocation properties or systemicity in plants also protect foliar or other plant parts which are not directly contacted with a compound of Formula 1, 1a or 1b or a composition comprising the compound.

Also noteworthy as embodiments of the present invention are compositions comprising a compound of any of the preceding Embodiments, as well as any other embodiments described herein, and any combinations thereof, and at least one additional component selected from the group consisting of a surfactant, a solid diluent and a liquid diluent, said compositions optionally further comprising at least one additional biologically active compound or agent.

Further noteworthy as embodiments of the present invention are compositions for controlling a parasitic nematode comprising a compound of any of the preceding Embodiments, as well as any other embodiments described herein, and any combinations thereof, and at least one additional component selected from the group consisting of a surfactant, a solid diluent and a liquid diluent, said compositions optionally further comprising at least one additional biologically active compound or agent. Embodiments of the invention further include methods for controlling a parasitic nematode comprising contacting the parasitic nematode or its environment with a biologically effective amount of a compound of any of the preceding Embodiments (e.g., as a composition described herein).

Embodiments of the invention also include a composition comprising a compound of any of the preceding Embodiments, in the form of a soil drench liquid formulation. Embodiments of the invention further include methods for controlling a parasitic nematode comprising contacting the soil with a liquid composition as a soil drench comprising a biologically effective amount of a compound of any of the preceding Embodiments.

Embodiments of the invention also include a spray composition for controlling a parasitic nematode comprising a biologically effective amount of a compound of any of the preceding Embodiments and a propellant. Embodiments of the invention further include a bait composition for controlling a parasitic nematode comprising a biologically effective amount of a compound of any of the preceding Embodiments, one or more food materials, optionally an attractant, and optionally a humectant.

Embodiments of the invention also include methods for protecting a seed from a parasitic nematode comprising contacting the seed with a biologically effective amount of a compound of any of the preceding Embodiments.

Embodiments of the invention also include methods for controlling a parasitic nematode comprising contacting the parasitic nematode or its environment with a biologically effective amount of a compound of Formula 1, 1a, 1b or 2 (e.g., as a composition described herein), provided that the methods are not methods of medical treatment of a human or animal body by therapy.

This invention also relates to such methods wherein the parasitic nematode or its environment is contacted with a composition comprising a biologically effective amount of a compound of Formula 1, 1a, 1b or 2, and at least one additional component selected from the group consisting of surfactants, solid diluents and liquid diluents, said composition optionally further comprising a biologically effective amount of at least one additional biologically active compound or agent, provided that the methods are not methods of medical treatment of a human or animal body by therapy.

One or more of the following methods and variations as described in Schemes 1-3 can be used to prepare the compounds of Formulae 1, 1a, 1b and 2. The definitions of Q, $R^{1a}$, $R^{1b}$, $R^2$, $R^3$ and $R^4$ in the compounds of Formulae 2-8b below are as defined above in the Summary of the Invention unless otherwise noted. Room temperature is between about 20 and 25° C.

Compounds of Formula 2 can be prepared by the reaction of compounds of Formula 3, wherein LG is a leaving group such as halogen, with amines of Formula 4 as shown in Scheme 1. When LG is halogen, the reaction is typically conducted in the presence of a base and in a suitable solvent. Suitable bases include amines such as triethylamine, pyridine and picoline, inorganic metal salts such as carbonates, bicarbonates, hydroxides and alkoxides, including sodium and potassium carbonate, sodium and potassium bicarbonate, sodium hydroxide and sodium ethoxide. The choice of a suitable solvent is dependent on the nature of LG, the base, and reaction conditions selected. Typical solvents include aliphatic hydrocarbons such as hexane, cyclohexane and heptane, aromatic hydrocarbons such as toluene and xylene, halogenated hydrocarbons such as dichloromethane, dichloroethane and chlorobenzene, ethers such as diethyl ether, tetrahydrofuran, dioxane and dimethoxyethane, esters such as ethyl acetate, amides such as DMF, DMAC and N-methylpyrrolidone, nitriles such as acetonitrile, ketones such as acetone and MEK, and polar protic solvents such as ethanol and water.

Scheme 1

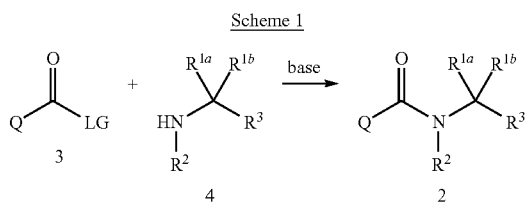

Compounds of Formula 2 can also be prepared by the reaction of compounds of Formula 5 with amines of Formula 4 as shown in Scheme 2. In this method, an amide coupling reagent such as HATU (1-[bis(dimethylamino)methylene]-1H-1,2,3-triazolo[4,5-b]pyridinium 3-oxide hexafluorophosphate), EDC (1-ethyl-3-(3-dimethylaminopropyl)carbodiimide) is used. Reaction conditions for these amide couplings are known in the art.

Scheme 2

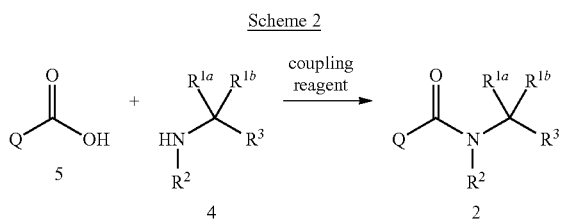

Compounds of Formula 1 are a subset of the compounds of Formula 2, and can be prepared in the manner described above for the preparation of compounds of Formula 2.

The enantiomeric structures of Formulae 1a and 1b can be prepared as shown in Scheme 3 by methods and conditions similar to those described in Schemes 1 and 2. For example, as shown in Scheme 3, coupling of furan of Formula 6 with either chiral amine of Formula 7a or 7b yields compounds of Formula 8a or 8b, respectively. Amines of Formulae 7a and 7b are commercially available or can be prepared by chiral resolution of the corresponding racemic amines by known methods.

Scheme 3

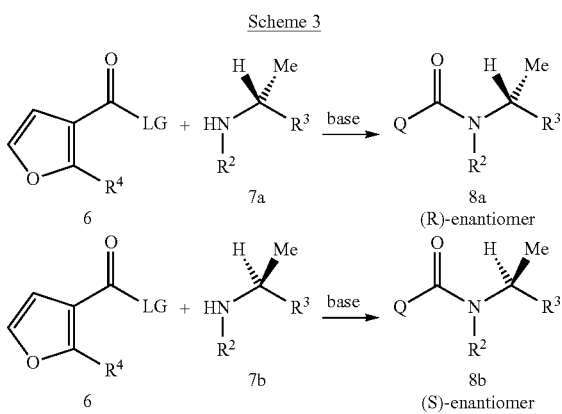

Alternatively, compounds of Formula 1 can be prepared as racemic mixtures, and the compounds of Formulae 1a and 1b can be separated into their respective enantiomers by chiral column chromatography. A large variety of chiral columns exist for separations of this type.

Compounds of Formulae 1, 1a, 1b and 2 wherein $R^2$ is other than H can also be prepared from their respective analogs wherein $R^2$ is H by reaction with the appropriately substituted alkyl, acyl or other reagent.

It is recognized that some reagents and reaction conditions described above for preparing compounds of Formula 1, 1a, 1b or 2 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis*, 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular sequence presented to prepare the compounds of Formula 1, 1a, 1b or 2.

One skilled in the art will also recognize that compounds of Formula 1, 1a, 1b or 2 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Synthesis Examples are, therefore, to be construed as merely illustrative, and not limiting of the disclosure in any way whatsoever. Steps in the following Synthesis Examples illustrate a procedure for each step in an overall synthetic transformation, and the starting material for each step may not have necessarily been prepared by a particular preparative run whose procedure is described in other Examples or Steps. $^1$H NMR spectra are reported in ppm downfield from tetramethylsilane; "s" means singlet, "d" means doublet, "dd" means doublet of doublets, "br s" means broad singlet. Room temperature is between about 20 and 25° C. "DMF" is N,N-dimethylformamide.

Synthesis Example 1

Preparation of 2-chloro-N-[(1S)-1-cyclopropylethyl]-3-furancarboxamide and 2-chloro-N-[(1R)-1-cyclopropylethyl]-3-furancarboxamide (compounds 11, 44 and 45)

Step A: Preparation of 2-chloro-3-furancarboxylic Acid

To a solution of diisopropylamine (10.3 g, 102 mmol) in THF (20 mL) was added 2.5M n-BuLi (6.5 g, 102 mmol) in hexane at −78° C. and the reaction mixture was slowly warmed to −40° C. 3-Furancarboxylic acid (5 g, 41 mmol) in THF (20 mL was then added and the reaction mixture was stirred for 30 minutes. Hexachloroethane (10.60 g, 45.68 mmol) in THF (20 mL) was slowly added at −78° C. and the reaction mixture was stirred for 16 hours. TLC analysis (5% MeOH in DCM) showed completion of the reaction. The reaction mixture was cooled to 0° C., quenched with 1N HCl, and extracted with ethyl acetate (3×). The combined organic layers were washed with brine and dried over $Na_2SO_4$. The solvent was evaporated under reduced pressure and the obtained crude product was purified by solvent washing to give 2.8 g of the title product as a brown solid. $^1$H NMR (CDCl$_3$, 400 MHz): δ 10.2 (br s, 1H), 7.33 (d, 1H), 6.81 (d, 1H). Mass spec: (M−1)=145.

Step B: Preparation of 2-chloro-N-[(1S)-1-cyclopropylethyl]-3-furancarboxamide and 2-chloro-N-[(1R)-1-cyclopropylethyl]-3-furancarboxamide To a solution of 2-chloro-3-furancarboxylic acid (1 g, 6.84 mmol) in DCM (25 mL) was added α-methylcyclopropanemethanamine hydrochloride (1:1) (0.75 g, 6.16 mmol), EDC-HCl (2 g, 10.27 mmol), DMAP (0.83 g 6.84 mmol), and the reaction mixture was stirred at room temperature for 6 hours, after which time TLC analysis (50% ethyl acetate in petroleum ether) showed completion of the reaction. The reaction mixture was quenched with water and extracted with ethyl acetate (3×). The combined organic layers were washed with water, brine, and then dried over $Na_2SO_4$. The solvent was evaporated under reduced pressure, and the crude product was purified on a silica gel column eluted with 20% ethyl acetate/petroleum ether to provide 0.7 g of the title compound as a white solid. $^1$H NMR (CDCl$_3$, 400 MHz): δ 7.31 (d, 1H), 6.82 (d, 1H), 6.19 (br s, 1H), 3.6 (m, 1H), 1.57 (d, 3H), 0.93 (m, 1H), 0.53 (m, 2H), 0.49 (m, 1H), 0.27 (m, 1H). Mass spec: (M+1)=214.

The 1S and 1R isomers were separated by chiral preparative HPLC, yielding two stereoisomers with optical rotations [α] of −21.5 and +21.2 (c 0.5, chloroform).

Synthesis Example 2

Preparation of 2-chloro-N-(1,2,2-trimethylpropyl)-3-furancarboxamide (compound 27)

Step A: Preparation of 2-chloro-3-furancarbonyl chloride

Under a nitrogen atmosphere, 2-chloro-3-furancarboxylic acid (1.0 g, 6.8 mmol) was suspended in 100 mL of anhydrous dichloromethane. Oxalylchloride (0.98 mL, 11.4 mmol) was then added followed by 1 drop of DMF. The reaction mixture was stirred overnight, and the solvent was subsequently removed under reduced pressure to yield 852 mg (76%) of a tan oil. $^1$H NMR (CDCl$_3$, 500 MHz): δ 7.37 (d, J=2.4 Hz, 1H), 6.89 ppm (d, J=2.2 Hz, 1H).

A stock solution was prepared [75 mg/5 mL] in dichloromethane to be used in further reactions.

Step B: Preparation of 2-chloro-N-(1,2,2-trimethylpropyl)-3-furancarboxamide

To a solution of 2-chloro-3-furancarbonyl chloride (100 mg, 0.61 mmol) in 6.6 mL of anhydrous dichloromethane was added 3-amino-2,2-dimethylbutane (90 μL, 0.67 mmol) under a nitrogen atmosphere. Triethylamine (136 μL, 0.98 mmol) was then added and the mixture stirred at room temperature overnight. The solution was then washed with water, concentrated in the presence of Celite®, and purified by chromatography (0-20% EtOAc:hexanes) to yield 64 mg (46%) of the title compound as a tan oil. $^1$H NMR (CDCl$_3$, 500 MHz): δ 7.32 (d, J=2.2 Hz, 1H), 6.85 (d, J=2.2 Hz, 1H), 6.12-6.20 (m, 1H), 4.05 (dq, J=9.5, 6.8 Hz, 1H), 1.15 (d, J=6.8 Hz, 3H), 0.84-1.06 ppm (s, 9H). LC/MS m/z [M+H]$^+$: 230.3.

Synthesis Example 2a

Preparation of 2-chloro-N-[(1S)-1,2,2-trimethylpropyl]-3-furancarboxamide (Compound 40)

Step A: Preparation of 2-chloro-N-[(1S)-1,2,2-trimethylpropyl]-3-furancarboxamide To a solution of 2-chloro-3-furancarbonyl chloride (75 mg, 0.46 mmol) in 5 mL of anhydrous dichloromethane was added (S)-(+)-3-amino-2,2-dimethylbutane (67 μL, 0.50 mmol) under a nitrogen atmosphere. Triethylamine (188 μL, 1.35 mmol) was then added and the mixture stirred at room temperature overnight. The solution was then washed with water, concentrated in the presence of Celite®, and purified by chromatography (0-20% EtOAc:hexanes) to yield 33 mg (31%) of the title compound as a white solid. $^1$H NMR (CDCl$_3$, 500 MHz): δ 7.32 (d, J=2.2 Hz, 1H), 6.85 (d, J=2.2 Hz, 1H), 6.12-6.20 (m, 1H), 4.05 (dq, J=9.5, 6.8 Hz, 1H), 1.15 (d, J=6.8 Hz, 3H), 0.84-1.06 ppm (s, 9H). LC/MS m/z [M+H]$^+$: 230.4. [α]+10.7° (c 3.65, methanol).

Synthesis Example 2b

Preparation of 2-chloro-N-[(1R)-1,2,2-trimethylpropyl]-3-furancarboxamide (Compound 41)

Step A: Preparation of 2-chloro-N-[(1R)-1,2,2-trimethylpropyl]-3-furancarboxamide To a solution of 2-chloro-3-furancarbonyl chloride (75 mg, 0.46 mmol) in 5 mL of anhydrous dichloromethane was added (R)-(+)-3-amino-2,2-dimethylbutane (67 μL, 0.50 mmol) under a nitrogen atmosphere. Triethylamine (188 μL, 1.35 mmol) was then added and the mixture stirred at room temperature overnight. The solution was then washed with water, concentrated in the presence of Celite®, and purified by chromatography (0-20% EtOAc:hexanes) to yield 38 mg (36%) of the title compound as a white solid. $^1$H NMR (CDCl$_3$, 500 MHz): δ 7.32 (d, J=2.2 Hz, 1H), 6.85 (d, J=2.2 Hz, 1H), 6.12-6.20 (m, 1H), 4.05 (dq, J=9.5, 6.8 Hz, 1H), 1.15 (d, J=6.8 Hz, 3H), 0.84-1.06 ppm (s, 9H). LC/MS m/z [M+H]$^+$: 230.3. [α] −9.09° (c 3.85, methanol).

Specific compounds of Formula 1, 1a, 1b or 2, prepared by the methods and variations as described in preceding Schemes 1-3 and Synthesis Example 1, 2, 2a and 2b, are shown in the Index Tables below. The following abbreviations may be used: Cmpd means Compound, t is tertiary, Me is methyl, and Et is ethyl. A "-" in a structure fragment denotes the attachment point of the fragment to the remainder of the molecule. The abbreviation "Ex." stands for "Example" and is followed by a number indicating in which Synthesis Example the compound is prepared.

Columns titled "MS" contain mass spectral data. Columns titled "MP" contain melting point range data. In instances where a single column is titled "MS/MP", an entry in this column consisting of a range (e.g., 120-122) represents a melting point range, while an entry in this column consisting of a single number (e.g., 208.1) represents mass spectral data. For mass spectral data, the numerical value reported is the molecular weight of the observed molecular ion formed by addition of H$^+$ (molecular weight of 1) to the molecule having the greatest isotopic abundance (i.e. M). The reported mass spectral peaks were observed by mass spectrometry using atmospheric pressure chemical ionization (AP$^+$).

INDEX TABLE A

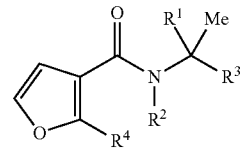

R$^4$ is Me

| Compd. No. | R$^1$ | R$^2$ | R$^3$ | MS | MP |
|---|---|---|---|---|---|
| 1 | H | H | —CH(Me)Et | | 75-78 |
| 2 | H | Me | cyclopropyl | 208.1 | |
| 3 | H | H | methyl | | 80-83 |
| 4 | H | H | isopropyl | | 68-71 |
| 5 | H | H | propyl | * | * |
| 6 | H | H | cyclopropyl | | 64-68 |
| 7 | Me | H | cyclopropyl | | 78-82 |
| 80 | H | H | —CH$_2$C(Me)$_3$ | | 104-108 |

R$^4$ is Cl

| Compd. No. | R$^1$ | R$^2$ | R$^3$ | MS | MP |
|---|---|---|---|---|---|
| 8 | Me | H | cyclopropyl | | 62-63 |
| 9 | H | H | —CH$_2$CH$_2$(cyclopropyl) | 242.1 | |
| 10 | Me | H | isopropyl | 230.3 | |
| 11 (Ex. 1) | H | H | cyclopropyl | | 82-86 |
| 12 | Me | H | —CH$_2$OMe | * | * |
| 13 | H | H | —CH$_2$OMe | | 55-56 |
| 14 | Me | H | —CH$_2$SMe | | 59-60 |
| 15 | Me | H | —CH$_2$SO$_2$Me | | 100-101 |
| 16 | H | H | ethyl | | 85-86 |
| 17 | H | H | propyl | * | * |
| 18 | Me | H | —CH$_2$C(Me)$_3$ | * | * |
| 19 | H | H | —CH$_2$CH(Me)$_2$ | 230.3 | |
| 20 | H | H | cyclopentyl | 242.4 | |
| 21 | H | H | cyclohexyl | 256.4 | |
| 22 | H | H | 1-methylcyclopropyl | 228.3 | |
| 23 | H | H | cyclobutyl | 228.3 | |
| 24 | H | H | —CF$_3$ | 242.3 | |
| 25 | Me | H | —CH$_2$S(O)Me | | 134-135 |
| 26 | H | H | isopropyl | | 81-84 |
| 27 (Ex. 2) | H | H | t-butyl | 230.4 | |
| 28 | H | H | —CH$_2$SMe | 234.3 | |
| 29 | H | H | pentyl | 244.4 | |
| 30 | H | H | 4-methylpentyl | 258.4 | |
| 31 | H | Me | cyclopropyl | 229.2 | |
| 78 | H | H | —CH$_2$C(Me)$_3$ | 244.3 | |

R$^4$ is Br

| Compd. No. | R$^1$ | R$^2$ | R$^3$ | MS | MP |
|---|---|---|---|---|---|
| 32 | H | H | cyclopropyl | | 54-57 |
| 33 | H | H | isopropyl | | 58-59 |
| 34 | H | H | propyl | * | * |
| 35 | H | H | t-butyl | * | * |

-continued

INDEX TABLE A

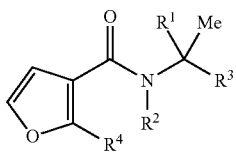

R⁴ is CN

| Compd. No. | R¹ | R² | R³ | MS |
|---|---|---|---|---|
| 79 | H | H | —C(Me)₂Et | 235.2 |
| 97 | H | H | —CH₂C(Me)₃ | * |
| 98 | H | H | —CH₂CH(Me)₂ | * |

R⁴ is I

| Compd. No. | R¹ | R² | R³ | MS | MP |
|---|---|---|---|---|---|
| 83 | H | H | —CH₂C(Me)₃ |  | 68-72 |
| 88 | H | H | t-butyl | 322.4 |  |

* See Index Table D for ¹H NMR data.

INDEX TABLE B-1

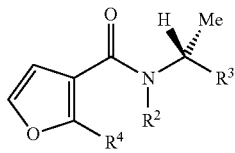

R⁴ is Me

| Cmpd. No. | R³ | MP | Optical Rotation |
|---|---|---|---|
| 36 | cyclopropyl | 70-73 |  |
| 39 | t-butyl | 63-64 |  |
| 84 | —CH₂C(Me)₃ | 130-134 | −30.35 (c 0.1, chloroform) |
| 96 | isopropyl | 51-55 |  |

R⁴ is Cl

| Cmpd. No. | R³ | MS | MP | Optical Rotation |
|---|---|---|---|---|
| 41 (Ex. 2b) | t-butyl | 230.3 |  | −9.09 (c 3.85, methanol) |
| 45 (Ex. 1) | cyclopropyl |  | 144-148 | −21.5 (c 0.1, chloroform) |
| 75 | isopropyl | 216.1 |  | −20.0 (c 0.1, chloroform) |
| 76 | ethyl |  | 64-65 |  |

R⁴ is Br

| Cmpd. No. | R³ | MP | Optical Rotation |
|---|---|---|---|
| 38 | t-butyl | 89-90 |  |
| 74 | cyclopropyl | 70-73 |  |

R⁴ is I

| Cmpd. No. | R³ | MS | MP | Optical Rotation |
|---|---|---|---|---|
| 86 | t-butyl | 322.1 |  | −12.66 (c 0.4, chloroform) |
| 102 | —CH₂C(Me)₃ |  | 94-98 | −22.8 (c 0.25, chloroform) |

INDEX TABLE B-2

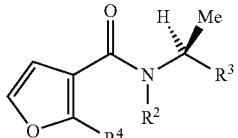

$R^4$ is Me

| Cmpd. No. | $R^3$ | MS | MP | Optical Rotation |
|---|---|---|---|---|
| 37 | cyclopropyl | | 70-73 | |
| 85 | —CH$_2$C(Me)$_3$ | | 132-136 | +23.62 (c 0.25, chloroform) |
| 94 | t-butyl | 213.4 | | |
| 101 | isopropyl | | 53-54 | |

$R^4$ is Cl

| Cmpd. No. | $R^3$ | MS | MP | Optical Rotation |
|---|---|---|---|---|
| 40 (Ex. 2a) | t-butyl | 230.4 | | +10.7 (c 3.65, methanol) |
| 43 | isopropyl | * | * | +22.0 (c 0.1, chloroform) |

INDEX TABLE B-2 -continued

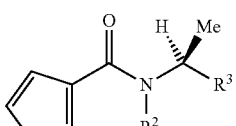

| | | | | |
|---|---|---|---|---|
| 44 (Ex. 1) | cyclopropyl | | 81-85 | +21.2 (c 0.1, chloroform) |
| 77 | ethyl | | 64-65 | |

$R^4$ is Br

| Cmpd. No. | $R^3$ | | MP | Optical Rotation |
|---|---|---|---|---|
| 42 | t-butyl | | 90-91 | |
| 73 | cyclopropyl | | 71-75 | |

$R^4$ is I

| Cmpd. No. | $R^3$ | MS | MP | Optical Rotation |
|---|---|---|---|---|
| 87 | t-butyl | 322.1 | | +19.2 (c 0.5, chloroform) |
| 103 | —CH$_2$C(Me)$_3$ | | 92-96 | +111.2 (c 0.25, chloroform) |

* See Index Table D for $^1$H NMR data.

INDEX TABLE C-1

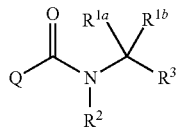

| Comp. No. | | $R^{1a}$ | $R^{1b}$ | $R^3$ | MS/MP |
|---|---|---|---|---|---|
| 46 | 2-methyl-3-furanyl | cyclopropyl | H | cyclopropyl | 110-115 |
| 47 | 2-methyl-3-furanyl | —CH$_2$CH$_2$— | | cyclopropyl | * |
| 48 | 3-methyl-2-thienyl | Me | H | isopropyl | 84-88 |
| 49 | 3-fluoro-2-thienyl | Me | H | cyclopropyl | 72-76 |
| 50 | 3-bromo-2-thienyl | Me | H | cyclopropyl | 41-44 |
| 51 | 2-chloro-3-furanyl | —CH$_2$CH$_2$— | | cyclopropyl | 82-83 |
| 52 | 3-methyl-2-thienyl | cyclopropyl | H | cyclopropyl | 121-125 |
| 53 | 2-chloro-3-furanyl | ethyl | H | cyclopropyl | 74-77 |
| 54 | 2-chloro-3-furanyl | ethyl | H | —CH$_2$OMe | 54-55 |
| 55 | 5-iodo-2-methyl-4-thiazolyl | methyl | H | cyclopropyl | 337.3 |
| 56 | 5-iodo-4-thiazolyl | methyl | H | cyclopropyl | 323.3 |
| 57 | 2-chloro-4-iodo-5-thiazolyl | methyl | H | cyclopropyl | 357.2 |
| 58 | 3-methylthio-2-thienyl | methyl | H | cyclopropyl | 242.3 |
| 59 | 2-bromo-5-thiazolyl | methyl | H | cyclopropyl | 277.2 |
| 60 | 2-methyl-5-thiazolyl | methyl | H | cyclopropyl | 211.3 |
| 61 | 5-thiazolyl | methyl | H | cyclopropyl | 197.3 |
| 62 | 5-chloro-4-thiazolyl | methyl | H | cyclopropyl | 231.3 |
| 63 | 5-bromo-4-thiazolyl | methyl | H | cyclopropyl | 275.2 |
| 64 | 3-methoxy-2-thienyl | methyl | H | cyclopropyl | 60-62 |
| 65 | 3-(trifluoromethyl)-2-thienyl | methyl | H | cyclopropyl | 65-68 |
| 66 | 2-chloro-3-furanyl | cyclopropyl | H | trifluoromethyl | 101-106 |
| 67 | 2-methyl-3-furanyl | ethyl | H | cyclopropyl | 76-80 |
| 68 | 3-chloro-2-thienyl | cyclopropyl | H | cyclopropyl | 160-164 |
| 69 | 2-thienyl | methyl | H | cyclopropyl | 143-146 |
| 70 | 4-methyl-5-thiazolyl | methyl | H | cyclopropyl | 211.4 |
| 71 | 4-thiazolyl | methyl | H | cyclopropyl | 197.3 |
| 72 | 5-(trifluoromethyl)-4-thiazolyl | methyl | H | cyclopropyl | 265.3 |
| 82 | 4-methyl-5-thiazolyl | methyl | H | t-butyl | 114-118 |
| 89 | 3-(1,1-dimethylethyl)-2-thienyl | methyl | H | isopropyl | 67-68 |
| 90 | 3-(1,1-dimethylethyl)-2-thienyl | methyl | H | t-butyl | 68-69 |

INDEX TABLE C-1

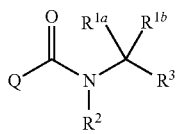

| Comp. No. | Q | $R^{1a}$ | $R^{1b}$ | $R^3$ | MS/MP |
|---|---|---|---|---|---|
| 93 | 5-bromo-4-thiazolyl | methyl | methyl | —CH$_2$OMe | 293.2 |
| 99 | 2-methyl-3-furanyl | t-butyl | H | t-butyl | 285.1 |

* See Index Table D for $^1$H NMR data.

INDEX TABLE C-2

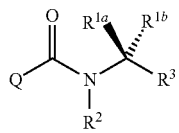

$R^2$ is H

| Cmpd. No. | Q | $R^{1a}$ | $R^{1b}$ | $R^3$ | MS/MP | Optical Rotation |
|---|---|---|---|---|---|---|
| 81 | 4-methyl-5-thiazolyl | Me | H | t-butyl | 125-129 | +33.9 (c 0.1, chloroform) |
| 91 | 3-(1,1dimethylethyl)-2-thienyl | H | Me | t-butyl | 42-43 | −33.1 (c 0.8, chloroform) |
| 92 | 3-(1,1dimethylethyl)-2-thienyl | Me | H | t-butyl | 54-55 | +17.3 (c 0.79, chloroform) |
| 95 | 3-cyano-2-thienyl | Me | H | t-butyl | 237.3 | +26.4 (c 0.78, chloroform) |
| 100 | 4-methyl-3-thienyl | Me | H | t-butyl | 210.3 | −35.1 (c 0.77, chloroform) |

INDEX TABLE D

| Cmpd. No. | $^1$H NMR Data $^a$ |
|---|---|
| 5 | $^1$H NMR (CDCl$_3$) δ 7.26 (s, 1H), 6.41 (s, 1H), 5.44 (br s, 1H), 4.15 (m, 1H), 2.58 (s, 3H), 1.50 (m, 2H), 1.30 (m, 2H), 1.20 (d, 3H), 0.93 (t, 3H). |
| 12 | $^1$H NMR (CDCl$_3$) δ 7.29 (d, 1H), 6.78 (s, 1H), 6.50 (br s, 1H), 3.41 (s, 3H), 3.41 (s, 2H), 1.45 (s, 6H). |
| 17 | $^1$H NMR (CDCl$_3$) δ 7.31 (s, 1H), 6.82 (s, 1H), 6.00 (br s, 1H), 4.18 (m, 1H), 1.5 (m, 2H), 1.30 (m, 2H), 1.22 (d, 1H), 0.95 (t, 3H). |
| 18 | $^1$H NMR (CDCl$_3$) δ 7.31 (s, 1H), 6.82 (s, 1H), 6.20 (br s, 1H), 1.85 (s, 2H), 1.50 (s, 6H), 1.02 (s, 9H). |
| 34 | $^1$H NMR (CDCl$_3$) δ 7.45 (s, 1H), 6.80 (s, 1H), 6.05 (br s, 1H), 4.18 (m, 1H), 1.50 (m, 2H), 1.30 (m, 2H), 1.23 (d, 3H), 0.95 (t, 3H). |
| 35 | $^1$H NMR (CDCl$_3$) δ 7.46 (s, 1H), 6.87 (s, 1H), 6.22 (br s, 1H), 4.07 (m, 1H), 1.17 (d, 3H), 0.97 (d, 6H). |
| 43 | $^1$H NMR (CDCl$_3$) δ 7.32 (s, 1H), 6.84 (s, 1H), 6.25 (br s, 1H), 4.06 (m, 1H), 1.79 (m, 1H), 1.17 (d, 3H), 0.96 (d, 6H). |
| 47 | $^1$H NMR (CDCl$_3$) δ 7.08 (s, 1H), 6.23 (s, 1H), 6.00 (br s, 1H), 2.42 (s, 3H), 1.35 (m, 1H), 0.60 (m, 2H), 0.50 (m, 2H), 0.28 (m, 2H), 0.02 (m, 2H). |
| 97 | $^1$H NMR (CDCl$_3$) δ 7.46 (s, 1H), 6.47 (s, 1H), 5.24 (br s, 1H), 4.13 (m, 1H), 1.49-1.42 (m, 2H), 1.24-1.19 (m, 3H), 0.95 (s, 9H). |
| 98 | $^1$H NMR (CDCl$_3$) δ 7.42 (s, 1H), 6.59 (br s, 1H), 4.24-4.20 (m, 1H), 1.63 (m, 1H), 1.55-1.44 (m, 1H), 1.35-1.28 (m, 1H), 1.21 (d, 3H), 0.92-0.91 (m, 6H). |

$^a$ $^1$H NMR data are in ppm downfield from tetramethylsilane. Couplings are designated by (s)-singlet, (br s)-broad singlet, (d)-doublet, (t)-triplet, (m)-multiplet, (dd)-doublet of doublets, (dt)-doublet of triplets, (br)-broad.

A compound of this invention will generally be used as a parasitic nematode control active ingredient in a composition, i.e. formulation, with at least one additional component selected from the group consisting of surfactants, solid diluents and liquid diluents, which serves as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions and/or suspo-emulsions) and the like, which optionally can be thickened into gels. The general types of aqueous liquid compositions are soluble concentrate, suspension concentrate, capsule suspension, concentrated emulsion, microemulsion and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, prills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water. Spray volumes can range from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting. Liquid and solid formulations can be applied onto seeds of crops and other desirable vegetation as seed treatments before planting to protect developing roots and other subterranean plant parts and/or foliage through systemic uptake.

The formulations will typically contain effective amounts of active ingredient, diluent and surfactant within the following approximate ranges which add up to 100 percent by weight.

|  | Weight Percent | | |
| --- | --- | --- | --- |
|  | Active Ingredient | Diluent | Surfactant |
| Water-Dispersible and Water-soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-95 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers*, 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, triacetin, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol and benzyl alcohol. Liquid diluents also include glycerol esters of saturated and unsaturated fatty acids (typically $C_6$-$C_{22}$), such as plant seed and fruit oils (e.g, oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide*, 2nd Ed., Interscience, New York, 1950.

The solid and liquid compositions of the present invention often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons, New York, 1987.

Compositions of this invention may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

The compound of Formula 1, 1a, 1b or 2 and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 μm can be wet milled using media mills to obtain particles with average diameters below 3 μm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 μm range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. Nos. 4,144,050, 3,920,442 and DE 3,246,493. Tablets can be prepared as taught in U.S. Pat. Nos. 5,180,587, 5,232,701 and 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, U K, 2000.

In the following Examples, all formulations are prepared in conventional ways. Compound numbers refer to compounds in Index Tables. Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except where otherwise indicated.

Example A

High Strength Concentrate

| | |
|---|---|
| compound 9 | 98.5% |
| silica aerogel | 0.5% |
| synthetic amorphous fine silica | 1.0% |

Example B

Wettable Powder

| | |
|---|---|
| compound 11 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

Example C

Granule

| | |
|---|---|
| compound 26 | 10.0% |
| attapulgite granules (low volatile matter, 0.71/0.30 mm; U.S.S. No. 25-50 sieves) | 90.0% |

Example D

Extruded Pellet

| | |
|---|---|
| compound 40 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

Example E

Emulsifiable Concentrate

| | |
|---|---|
| compound 43 | 10.0% |
| polyoxyethylene sorbitol hexoleate | 20.0% |
| $C_6$-$C_{10}$ fatty acid methyl ester | 70.0% |

Example F

Microemulsion

| | |
|---|---|
| compound 78 | 5.0% |
| polyvinylpyrrolidone-vinyl acetate copolymer | 30.0% |
| alkylpolyglycoside | 30.0% |
| glyceryl monooleate | 15.0% |
| water | 20.0% |

Example G

Seed Treatment

| | |
|---|---|
| compound 80 | 20.00% |
| polyvinylpyrrolidone-vinyl acetate copolymer | 5.00% |
| montan acid wax | 5.00% |
| calcium ligninsulfonate | 1.00% |
| polyoxyethylene/polyoxypropylene block copolymers | 1.00% |
| stearyl alcohol (POE 20) | 2.00% |
| polyorganosilane | 0.20% |
| colorant red dye | 0.05% |
| water | 65.75% |

Example H

Fertilizer Stick

| | |
|---|---|
| compound 84 | 2.5% |
| pyrrolidone-styrene copolymer | 4.8% |
| tristyrylphenyl 16-ethoxylate | 2.3% |
| talc | 0.8% |
| corn starch | 5.0% |
| slow-release fertilizer | 36.0% |
| kaolin | 38.0% |
| water | 10.6% |

Example I

Suspension Concentrate

| | |
|---|---|
| compound 9 | 35% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| water | 53.7% |

Example J

Emulsion in Water

| | |
|---|---|
| compound 11 | 10.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| aromatic petroleum based hydrocarbon | 20.0 |
| water | 58.7% |

Example K

Oil Dispersion

| | |
|---|---|
| compound 26 | 25% |
| polyoxyethylene sorbitol hexaoleate | 15% |

-continued

| | |
|---|---|
| organically modified bentonite clay | 2.5% |
| fatty acid methyl ester | 57.5% |

Example L

Suspoemulsion

| | |
|---|---|
| compound 40 | 10.0% |
| imidacloprid | 5.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| aromatic petroleum based hydrocarbon | 20.0% |
| water | 53.7% |

These present compounds and compositions are thus useful agronomically for protecting field crops from parasitic nematodes, and also nonagronomically for protecting other horticultural crops and plants from phytophagous parasitic nematodes. This utility includes protecting crops and other plants (i.e. both agronomic and nonagronomic) that contain genetic material introduced by genetic engineering (i.e. transgenic) or modified by mutagenesis to provide advantageous traits. Examples of such traits include tolerance to herbicides, resistance to phytophagous pests (e.g., insects, mites, aphids, spiders, nematodes, snails, plant-pathogenic fungi, bacteria and viruses), improved plant growth, increased tolerance of adverse growing conditions such as high or low temperatures, low or high soil moisture, and high salinity, increased flowering or fruiting, greater harvest yields, more rapid maturation, higher quality and/or nutritional value of the harvested product, or improved storage or process properties of the harvested products. Transgenic plants can be modified to express multiple traits. Examples of plants containing traits provided by genetic engineering or mutagenesis include varieties of corn, cotton, soybean and potato expressing an insecticidal *Bacillus thuringiensis* toxin such as YIELD GARD®, KNOCKOUT®, STARLINK®, BOLLGARD®, NuCOTN® and NEWLEAF®, INVICTA RR2 PRO™, and herbicide-tolerant varieties of corn, cotton, soybean and rapeseed such as ROUNDUP READY®, LIBERTY LINK®, IMI®, STS® and CLEARFIELD®, as well as crops expressing N-acetyltransferase (GAT) to provide resistance to glyphosate herbicide, or crops containing the HRA gene providing resistance to herbicides inhibiting acetolactate synthase (ALS). The present compounds and compositions may interact synergistically with traits introduced by genetic engineering or modified by mutagenesis, thus enhancing phenotypic expression or effectiveness of the traits or increasing the parasitic nematode control effectiveness of the present compounds and compositions. In particular, the present compounds and compositions may interact synergistically with the phenotypic expression of proteins or other natural products toxic to parasitic nematodes to provide greater-than-additive control of these pests.

Compositions of this invention can also optionally comprise plant nutrients, e.g., a fertilizer composition comprising at least one plant nutrient selected from nitrogen, phosphorus, potassium, sulfur, calcium, magnesium, iron, copper, boron, manganese, zinc, and molybdenum. Of note are compositions comprising at least one fertilizer composition comprising at least one plant nutrient selected from nitrogen, phosphorus, potassium, sulfur, calcium and magnesium. Compositions of the present invention which further comprise at least one plant nutrient can be in the form of liquids or solids. Of note are solid formulations in the form of granules, small sticks or tablets. Solid formulations comprising a fertilizer composition can be prepared by mixing the compound or composition of the present invention with the fertilizer composition together with formulating ingredients and then preparing the formulation by methods such as granulation or extrusion. Alternatively solid formulations can be prepared by spraying a solution or suspension of a compound or composition of the present invention in a volatile solvent onto a previous prepared fertilizer composition in the form of dimensionally stable mixtures, e.g., granules, small sticks or tablets, and then evaporating the solvent.

Compounds of this invention can exhibit activity against a wide spectrum of parasitic nematodes that live or grow inside or feed on plants (e.g., foliage, fruit, stems, roots or seeds) or animals and humans (e.g., vascular or digestive systems or other tissues) and therefore damage growing and stored agronomic crops, forestry, greenhouse crops, ornamentals and nursery crops, or afflict animal and human health. Crops of particular interest are fruiting vegetables such as solanaceous and cucurbit crops, plantation crops such as banana and coffee, root crops such as potatoes, onion and carrots, and field crops such as tobacco, peanut, cotton, sugarcane and soybean.

Compounds of this invention can have activity on members of both classes Adenophorea and Secementea of the Phylum Nematoda, including economically important members of the orders Enoplida, Dorylaimida, Rhabditida, Strongylida, Ascarida, Oxyurida, Spirurida, Tylenchida and Aphelenchida, such as but not limited to economically important agricultural pests such as root-knot nematodes of the genus *Meloidogyne*, cyst nematodes of the genera *Heterodera* and *Globodera*, lesion nematodes of the genus *Pratylenchus*, reniform nematodes of the genus *Rotylenchulus*, burrowing nematodes of the genus *Radopholus*, sting nematodes of the genus *Belonolaimus*, spiral nematodes of the genera *Helicotylenchus* and *Scutellonema*, citrus nematodes of the genus *Tylenchulus*, stubby root nematodes of the genera *Trichodorus* and *Paratrichodorus*, dagger nematodes of the genus *Xiphinema*, stunt nematodes of the genus *Tylenchorhynchus*, needle nematodes of the genera *Longidorus* and *Paralongidorus*, lance nematodes of the genus *Hoplolaimus*, ring nematodes of the family Criconematidae, stem nematodes of the genera *Ditylenchus* and *Anguina*, and foliar/stem nematodes of the genera *Aphelenchoides* and *Rhadinaphelenchus*; and animal and human health parasites (i.e. economically important roundworms such as *Strongylus vulgaris* in horses, *Toxocara canis* in dogs, *Haemonchus contortus* in sheep, *Dirofilaria immitis* in dogs, etc.).

Of note is use of compounds of this invention for controlling southern root-knot nematode (*Meloidogyne incognita*). Those skilled in the art will appreciate that not all compounds are equally effective against all growth stages of all nematodes.

Compounds of this invention can also have activity on members of the Phylum Platyhelminthes, classes Cestoda (Tapeworms) and Trematoda (Flukes), including parasites (i.e. economically important flukes and tapeworms) afflicting animal and human health (e.g., *Anoplocephala perfoliata* in horses, *Fasciola hepatica* in ruminants, etc.).

Compounds of this invention can also be mixed with one or more other biologically active compounds or agents including insecticides, fungicides, nematocides, bactericides, acaricides, herbicides, herbicide safeners, growth regulators such as insect molting inhibitors and rooting stimulants, chemosterilants, semiochemicals, repellents, attractants, pheromones, feeding stimulants, other biologically active compounds or entomopathogenic bacteria, virus or fungi to form a multi-component pesticide giving an even broader spectrum of agronomic and nonagronomic utility. Thus the present invention also pertains to a composition comprising a compound of Formula 1, 1a or 1b, and an effective amount of at least one additional biologically active compound or agent and can further comprise at least one of surfactants, solid diluents or liquid diluents. For mixtures of the present invention, the other biologically active compounds or agents can be formulated together with the present compounds, including the compounds of Formula 1, 1a or 1b, to form a premix, or the other biologically active compounds or agents can be formulated separately from the present compounds, including the compounds of Formula 1, 1a or 1b, and the two formulations combined together before application (e.g., in a spray tank) or, alternatively, applied in succession.

Examples of such biologically active compounds or agents with which compounds of this invention can be formulated are insecticides such as abamectin, acephate, acequinocyl, acetamiprid, acrinathrin, afidopyropen ([(3S,4R,4aR,6S,6aS,12R,12aS,12bS)-3-[(cyclopropylcarbonyl)oxy]-1,3,4,4a,5,6,6a,12,12a,12b-decahydro-6,12-dihydroxy-4,6a, 12b-trimethyl-11-oxo-9-(3-pyridinyl)-2H,11H-naphtho[2,1-b]pyrano[3,4-e]pyran-4-yl]methyl cyclopropanecarboxylate), amidoflumet, amitraz, avermectin, azadirachtin, azinphos-methyl, benfuracarb, bensultap, bifenthrin, bifenazate, bistrifluron, borate, buprofezin, cadusafos, carbaryl, carbofuran, cartap, carzol, chlorantraniliprole, chlorfenapyr, chlorfluazuron, chlorpyrifos, chlorpyrifos-methyl, chromafenozide, clofentezin, clothianidin, cyantraniliprole (3-bromo-1-(3-chloro-2-pyridinyl)-N-[4-cyano-2-methyl-6-[(methylamino)carbonyl]phenyl]-1H-pyrazole-5-carboxamide), cyclaniliprole (3-bromo-N-[2-bromo-4-chloro-[[(1-cyclopropylethyl)amino]carbonyl]phenyl]-1-(3-chloro-2-pyridinyl)-1H-pyrazole-5-carboxamide), cycloprothrin, cycloxaprid ((5S,8R)-1-[(6-chloro-3-pyridinyl)methyl]-2,3,5,6,7,8-hexahydro-9-nitro-5,8-epoxy-1H-imidazo[1,2-a]azepine), cyflumetofen, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, diafenthiuron, diazinon, dieldrin, diflubenzuron, dimefluthrin, dimehypo, dimethoate, dinotefuran, diofenolan, emamectin, endosulfan, esfenvalerate, ethiprole, etofenprox, etoxazole, fenbutatin oxide, fenitrothion, fenothiocarb, fenoxycarb, fenpropathrin, fenvalerate, fipronil, flometoquin (2-ethyl-3,7-dimethyl-6-[4-(trifluoromethoxy)phenoxy]-4-quinolinyl methyl carbonate), flonicamid, flubendiamide, flucythrinate, flufenerim, flufenoxuron, flufenoxystrobin (methyl (αE)-2-[[2-chloro-4-(trifluoromethyl)phenoxy]methyl]-α-(methoxymethylene)benzeneacetate), fluensulfone (5-chloro-2-[(3,4,4-trifluoro-3-buten-1-yl)sulfonyl]thiazole), fluhexafon, fluopyram, flupiprole (1-[2,6-dichloro-4-(trifluoromethyl)phenyl]-5-[(2-methyl-2-propen-1-yl)amino]-4-[(trifluoromethyl)sulfinyl]-1H-pyrazole-3-carbonitrile), flupyradifurone (4-[[(6-chloro-3-pyridinyl)methyl](2,2-difluoroethyl)amino]-2(5H)-furanone), fluvalinate, tau-fluvalinate, fonophos, formetanate, fosthiazate, halofenozide, heptafluthrin ([2,3,5,6-tetrafluoro-4-(methoxymethyl)phenyl]methyl 2,2-dimethyl-3-[(1Z)-3,3,3-trifluoro-1-propen-1-yl]cyclopropanecarboxylate), hexaflumuron, hexythiazox, hydramethylnon, imidacloprid, indoxacarb, insecticidal soaps, isofenphos, lufenuron, malathion, meperfluthrin ([2,3,5,6-tetrafluoro-4-(methoxymethyl)phenyl]methyl (1R,3S)-3-(2,2-dichloroethenyl)-2,2-dimethylcyclopropanecarboxylate), metaflumizone, metaldehyde, methamidophos, methidathion, methiocarb, methomyl, methoprene, methoxychlor, methoxyfenozide, metofluthrin, monocrotophos, monofluorothrin ([2,3,5,6-tetrafluoro-4-(methoxy methyl)phenyl]methyl 3-(2-cyano-1-propen-1-yl)-2,2-dimethylcyclopropanecarboxylate), nicotine, nitenpyram, nithiazine, novaluron, noviflumuron, oxamyl, parathion, parathion-methyl, permethrin, phorate, phosalone, phosmet, phosphamidon, pirimicarb, profenofos, profluthrin, propargite, protrifenbute, pyflubumide (1,3,5-trimethyl-N-(2-methyl-1-oxopropyl)-N-[3-(2-methylpropyl)-4-[2,2,2-trifluoro-1-methoxy-1-(trifluoromethyl)ethyl]phenyl]-1H-pyrazole-4-carboxamide), pymetrozine, pyrafluprole, pyrethrin, pyridaben, pyridalyl, pyrifluquinazon, pyriminostrobin (methyl (αE)-2-[[[2-[(2,4-dichlorophenyl)amino]-6-(trifluoromethyl)-4-pyrimidinyl]oxy]methyl]-α-(methoxymethylene)benzeneacetate), pyriprole, pyriproxyfen, rotenone, ryanodine, silafluofen, spinetoram, spinosad, spirodiclofen, spiromesifen, spirotetramat, sulprofos, sulfoxaflor (N-[methyloxido[1-[6-(trifluoromethyl)-3-pyridinyl]ethyl]-$\lambda^4$-sulfanylidene]cyanamide), tebufenozide, tebufenpyrad, teflubenzuron, tefluthrin, terbufos, tetrachlorvinphos, tetramethrin, tetramethylfluthrin ([2,3,5,6-tetrafluoro-4-(methoxymethyl)phenyl]methyl 2,2,3,3-tetramethylcyclopropanecarboxylate), tetraniliprole, thiacloprid, thiamethoxam, thiodicarb, thiosultap-sodium, tioxazafen (3-phenyl-5-(2-thienyl)-1,2,4-oxadiazole), tolfenpyrad, tralomethrin, triazamate, trichlorfon, triflumezopyrim (2,4-dioxo-1-(5-pyrimidinylmethyl)-3-[3-(trifluoromethyl)phenyl]-2H-pyrido[1,2-a]pyrimidinium inner salt), triflumuron, *Bacillus thuringiensis* delta-endotoxins, entomopathogenic bacteria, entomopathogenic viruses and entomopathogenic fungi.

Of note are insecticides such as abamectin, acetamiprid, acrinathrin, afidopyropen, amitraz, avermectin, azadirachtin, benfuracarb, bensultap, bifenthrin, buprofezin, cadusafos, carbaryl, cartap, chlorantraniliprole, chlorfenapyr, chlorpyrifos, clothianidin, cyantraniliprole, cyclaniliprole, cycloprothrin, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, dieldrin, dinotefuran, diofenolan, emamectin, endosulfan, esfenvalerate, ethiprole, etofenprox, etoxazole, fenitrothion, fenothiocarb, fenoxycarb, fenvalerate, fipronil, flometoquin, flonicamid, flubendiamide, flufenoxuron, flufenoxystrobin, fluensulfone, flupiprole, flupyradifurone, fluvalinate, formetanate, fosthiazate, heptafluthrin, hexaflumuron, hydramethylnon, imidacloprid, indoxacarb, lufenuron, meperfluthrin, metaflumizone, methiocarb, methomyl, methoprene, methoxyfenozide, metofluthrin, monofluorothrin, nitenpyram, nithiazine, novaluron, oxamyl, pyflubumide, pymetrozine, pyrethrin, pyridaben, pyridalyl, pyriminostrobin, pyriproxyfen, ryanodine, spinetoram, spinosad, spirodiclofen, spiromesifen, spirotetramat, sulfoxaflor, tebufenozide, tetramethrin, tetramethylfluthrin, thiacloprid, thiamethoxam, thiodicarb, thiosultap-sodium, tralomethrin, triazamate, triflumezopyrim, triflumuron, *Bacillus thuringiensis* delta-endotoxins, all strains of *Bacillus thuringiensis* and all strains of nucleo polyhedrosis viruses.

One embodiment of biological agents for mixing with compounds of this invention include entomopathogenic bacteria such as *Bacillus thuringiensis*, and the encapsulated delta-endotoxins of *Bacillus thuringiensis* such as MVP® and MVPII® bioinsecticides prepared by the CellCap® process (CellCap®, MVP® and MVPII® are trademarks of Mycogen Corporation, Indianapolis, Ind., USA); entomopathogenic fungi such as green muscardine fungus; and entomopathogenic (both naturally occurring and genetically modified) viruses including baculovirus, nucleopolyhedro virus (NPV) such as *Helicoverpa zea* nucleopolyhedrovirus (HzNPV), Anagrapha falcifera nucleopolyhedrovirus (AfNPV); and granulosis virus (GV) such as Cydiapomonella granulosis virus (CpGV).

Of particular note is such a combination where the other invertebrate pest control active ingredient belongs to a different chemical class or has a different site of action than the compound of Formula 1, 1a or 1b. In certain instances, a combination with at least one other invertebrate pest control active ingredient having a similar spectrum of control but a different site of action will be particularly advantageous for resistance management. Thus, a composition of the present invention can further comprise at least one additional invertebrate pest control active ingredient having a similar spectrum of control but belonging to a different chemical class or having a different site of action. These additional biologically active compounds or agents include, but are not limited to, acetylcholinesterase (AChE) inhibitors such as the carbamates methomyl, oxamyl, thiodicarb, triazamate, and the organophosphates chlorpyrifos; GABA-gated chloride channel antagonists such as the cyclodienes dieldrin and endosulfan, and the phenylpyrazoles ethiprole and fipronil; sodium channel modulators such as the pyrethroids bifenthrin, cyfluthrin, beta-cyfluthrin, cyhalothrin, lambda-cyhalothrin, cypermethrin, deltamethrin, dimefluthrin, esfenvalerate, metofluthrin and profluthrin; nicotinic acetylcholinereceptor (nAChR) agonists such as the neonicotinoids acetamiprid, clothianidin, dinotefuran, imidacloprid, nitenpyram, nithiazine, thiacloprid, and thiamethoxam, and sulfoxaflor; nicotinic acetylcholine receptor (nAChR) allosteric activators such as the spinosyns spinetoram and spinosad; chloride channel activators such as the avermectins abamectin and emamectin; juvenile hormone mimics such as diofenolan, methoprene, fenoxycarb and pyriproxyfen; selective homopteran feeding blockers such as pymetrozine and flonicamid; mite growth inhibitors such as etoxazole; inhibitors of mitochondrial ATP synthase such as propargite; ucouplers of oxidative phosphorylation via disruption of the proton gradient such as chlorfenapyr; nicotinic acetylcholine receptor (nAChR) channel blockers such as the nereistoxin analogs cartap; inhibitors of chitin biosynthesis such as the benzoylureas flufenoxuron, hexaflumuron, lufenuron, novaluron, noviflumuron and triflumuron, and buprofezin; dipteran moulting disrupters such as cyromazine; ecdysone receptor agonists such as the diacylhydrazines methoxyfenozide and tebufenozide; octopamine receptor agonists such as amitraz; mitochondrial complex III electron transport inhibitors such as hydramethylnon; mitochondrial complex I electron transport inhibitors such as pyridaben; voltage-dependent sodium channel blockers such as indoxacarb; inhibitors of acetyl CoA carboxylase such as the tetronic and tetramic acids spirodiclofen, spiromesifen and spirotetramat; mitochondrial complex II electron transport inhibitors such as the ß-ketonitriles cyenopyrafen and cyflumetofen; ryanidine receptor modulators such as the anthranilic diamides chlorantraniliprole, cyantraniliprole and cyantraniliprole, diamides such as flubendiamide, and ryanodine receptor ligands such as ryanodine; compounds wherein the target site responsible for biological activity is unknown or uncharacterized such as azadirachtin, bifenazate, pyridalyl, pyrifluquinazon and triflumezopyrim; microbial disrupters of insect midgut membranes such as *Bacillus thuringensis* and the delta-endotoxins they produce and *Bacillus sphaericus*; and biological agents including nucleo polyhedro viruses (NPV) and other naturally occurring or genetically modified insecticidal viruses.

Further examples of biologically active compounds or agents with which compounds of this invention can be formulated are: fungicides such as acibenzolar-S-methyl, aldimorph, ametoctradin, amisulbrom, anilazine, azaconazole, azoxystrobin, benalaxyl (including benalaxyl-M), benodanil, benomyl, benthiavalicarb (including benthiavalicarb-isopropyl), benzovindiflupyr, bethoxazin, binapacryl, biphenyl, bitertanol, bixafen, blasticidin-S, boscalid, bromuconazole, bupirimate, buthiobate, carboxin, carpropamid, captafol, captan, carbendazim, chloroneb, chlorothalonil, chlozolinate, copper hydroxide, copper oxychloride, copper sulfate, coumoxystrobin, cyazofamid, cyflufenamid, cymoxanil, cyproconazole, cyprodinil, dichlofluanid, diclocymet, diclomezine, dicloran, diethofencarb, difenoconazole, diflumetorim, dimethirimol, dimethomorph, dimoxystrobin, diniconazole (including diniconazole-M), dinocap, dithianon, dithiolanes, dodemorph, dodine, econazole, etaconazole, edifenphos, enoxastrobin (also known as enestroburin), epoxiconazole, ethaboxam, ethirimol, etridiazole, famoxadone, fenamidone, fenaminstrobin, fenarimol, fenbuconazole, fenfuram, fenhexamide, fenoxanil, fenpiclonil, fenpropidin, fenpropimorph, fenpyrazamine, fentin acetate, fentin hydroxide, ferbam, ferimzone, flometoquin, fluazinam, fludioxonil, flufenoxystrobin, flumorph, fluopicolide, fluopyram, fluoxastrobin, fluquinconazole, flusilazole, flusulfamide, flutianil, flutolanil, flutriafol, fluxapyroxad, folpet, fthalide (also known as phthalide), fuberidazole, furalaxyl, furametpyr, hexaconazole, hymexazole, guazatine, imazalil, imibenconazole, iminoctadine albesilate, iminoctadine triacetate, iodicarb, ipconazole, isofetamid, iprobenfos, iprodione, iprovalicarb, isoprothiolane, isopyrazam, isotianil, kasugamycin, kresoxim-methyl, mancozeb, mandipropamid, mandestrobin, maneb, mapanipyrin, mepronil, meptyldinocap, metalaxyl (including metalaxyl-M/mefenoxam), metconazole, methasulfocarb, metiram, metominostrobin, metrafenone, myclobutanil, naftitine, neo-asozin (ferric methanearsonate), nuarimol, octhilinone, ofurace, orysastrobin, oxadixyl, oxathiapiprolin, oxolinic acid, oxpoconazole, oxycarboxin, oxytetracycline, penconazole, pencycuron, penflufen, penthiopyrad, perfurazoate, phosphorous acid (including salts thereof, e.g., fosetylaluminm), picarbutratox, picoxystrobin, piperalin, polyoxin, probenazole, prochloraz, procymidone, propamocarb, propiconazole, propineb, proquinazid, prothiocarb, prothioconazole, pyraclostrobin, pyrametostrobin, pyraoxystrobin, pyrazophos, pyribencarb, pyributacarb, pyrifenox, pyriofenone, perisoxazole, pyrimethanil, pyrifenox, pyrrolnitrin, pyroquilon, quinconazole, quinmethionate, quinoxyfen, quintozene, silthiofam, sedaxane, simeconazole, spiroxamine, streptomycin, sulfur, tebuconazole, tebufloquin, teclofthalam, tecloftalam, tecnazene, terbinafine, tetraconazole, thiabendazole, thifluzamide, thiophanate, thiophanate-methyl, thiram, tiadinil, tolclofos-methyl, tolprocarb, tolyfluanid, triadimefon, triadimenol, triarimol, triazoxide, tribasic copper sulfate, triclopyricarb, tridemorph, trifloxystrobin, triflumizole, trimoprhamide tricyclazole, triforine, triticonazole, uniconazole, validamycin, valifenalate (also known as valifenal), vinclozolin, zineb, ziram and zoxamide; nematocides such as fluopyram, spirotetramat, thiodicarb, fosthiazate, abamectin, iprodione, fluensulfone, dimethyl disulfide, tioxazafen, 1,3-dichloropropene (1,3-D), metam (sodium and potassium), dazomet, chloropicrin, fenamiphos, ethoprophos, cadusaphos, terbufos, imicyafos, oxamyl, carbofuran, tioxazafen, *Bacillus firmus* and *Pasteuria nishizawae*; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad.

In certain instances, combinations of a compound of this invention with other biologically active (particularly invertebrate pest control) compounds or agents (i.e. active ingredients) can result in a greater-than-additive (i.e. synergistic) effect. Reducing the quantity of active ingredients released in the environment while ensuring effective pest control is always desirable. When synergism with invertebrate pest control active ingredients occurs at application rates giving agronomically satisfactory levels of invertebrate pest control, such combinations can be advantageous for reducing crop production cost and decreasing environmental load.

Compounds of this invention and compositions thereof can be applied to plants genetically transformed to express proteins toxic to invertebrate pests (such as *Bacillus thuringiensis* delta-endotoxins). Such an application may provide a broader spectrum of plant protection and be advantageous for resistance management. The effect of the exogenously applied compounds of this invention may be synergistic with the expressed toxin proteins.

General references for these agricultural protectants (i.e. insecticides, fungicides, nematocides, acaricides, herbicides and biological agents) include *The Pesticide Manual,* 13*th Edition,* C. D. S. Tomlin, Ed., British Crop Protection Council, Farnham, Surrey, U. K., 2003 and *The BioPesticide Manual,* $2^{nd}$ *Edition,* L. G. Copping, Ed., British Crop Protection Council, Farnham, Surrey, U. K., 2001.

For embodiments where one or more of these various mixing partners are used, the weight ratio of these various mixing partners (in total) to a compound of Formula 1 is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components can expand the spectrum of parasitic nematodes controlled beyond the spectrum controlled by a compound of Formula 1 alone.

Parasitic nematodes are controlled in agronomic and nonagronomic applications by applying one or more compounds of this invention, typically in the form of a composition, in a biologically effective amount, to the environment of the pests, including the agronomic and/or nonagronomic locus of infestation, to the area to be protected, or directly on the pests to be controlled.

Thus the present invention comprises a method for controlling a parasitic nematode in agronomic and/or nonagronomic applications, comprising contacting the parasitic nematode or its environment with a biologically effective amount of one or more of the compounds of the invention, or with a composition comprising at least one such compound or a composition comprising at least one such compound and at least one additional biologically active compound or agent. Examples of suitable compositions comprising a compound of the invention and at least one additional biologically active compound or agent include granular compositions wherein the additional active compound is present on the same granule as the compound of the invention or on granules separate from those of the compound of the invention.

To achieve contact with a compound or composition of the invention to protect a field crop from parasitic nematodes, the compound or composition is typically applied to the seed of the crop before planting, to the foliage (e.g., leaves, stems, flowers, fruits) of crop plants, or to the soil or other growth medium before or after the crop is planted.

One embodiment of a method of contact is by spraying. Alternatively, a granular composition comprising a compound of the invention can be applied to the plant foliage or the soil. Compounds of this invention can also be effectively delivered through plant uptake by contacting the plant with a composition comprising a compound of this invention applied as a soil drench of a liquid formulation, a granular formulation to the soil, a nursery box treatment or a dip of transplants. Of note is a composition of the present invention in the form of a soil drench liquid formulation. Also of note is a method for controlling a parasitic nematode comprising contacting the parasitic nematode or its environment with a biologically effective amount of a compound of the present invention or with a composition comprising a biologically effective amount of a compound of the present invention. Of further note is this method wherein the environment is soil and the composition is applied to the soil as a soil drench formulation. Of further note is that compounds of this invention are also effective by localized application to the locus of infestation. Other methods of contact include application of a compound or a composition of the invention by direct and residual sprays, aerial sprays, gels, seed coatings, microencapsulations, systemic uptake, baits, ear tags, boluses, foggers, fumigants, aerosols, dusts and many others. One embodiment of a method of contact involves a dimensionally stable fertilizer granule, stick or tablet comprising a compound or composition of the invention. The compounds of this invention can also be impregnated into materials for fabricating invertebrate control devices (e.g., insect netting).

Compounds of this invention are also useful in seed treatments for protecting seeds from parasitic nematodes. In the context of the present disclosure and claims, treating a seed means contacting the seed with a biologically effective amount of a compound of this invention, which is typically formulated as a composition of the invention. This seed treatment protects the seed from invertebrate soil pests and generally can also protect roots and other plant parts in contact with the soil of the seedling developing from the germinating seed. The seed treatment may also provide protection of foliage by translocation of the compound of this invention or a second active ingredient within the developing plant. Seed treatments can be applied to all types of seeds, including those from which plants genetically transformed to express specialized traits will germinate. Representative examples of genetically transformed plants include those expressing proteins toxic to parasitic nematodes, such as *Bacillus thuringiensis* toxin or those expressing herbicide resistance such as glyphosate acetyltransferase, which provides resistance to glyphosate.

One method of seed treatment is by spraying or dusting the seed with a compound of the invention (i.e. as a formulated composition) before sowing the seeds. Compositions formulated for seed treatment generally comprise a film former or adhesive agent. Therefore typically a seed coating composition of the present invention comprises a biologically effective amount of a compound of Formula 1, 1a or 1b, and a film former or adhesive agent. Seed can be coated by spraying a flowable suspension concentrate directly into a tumbling bed of seeds and then drying the seeds. Alternatively, other formulation types such as wetted powders, solutions, suspo-emulsions, emulsifiable concentrates and emulsions in water can be sprayed on the seed. This process is particularly useful for applying film coatings on seeds. Various coating machines and processes are available to one skilled in the art. Suitable processes include those listed in P. Kosters et al., Seed Treatment: Progress and Prospects, 1994 BCPC Monograph No. 57, and references listed therein.

The treated seed typically comprises a compound of the present invention in an amount from about 0.1 g to 1 kg per 100 kg of seed (i.e. from about 0.0001 to 1% by weight of the seed before treatment). A flowable suspension formulated for seed treatment typically comprises from about 0.5 to about 70% of the active ingredient, from about 0.5 to about 30% of a film-forming adhesive, from about 0.5 to about 20% of a dispersing agent, from 0 to about 5% of a thickener, from 0 to about 5% of a pigment and/or dye, from 0 to about 2% of an antifoaming agent, from 0 to about 1% of a preservative, and from 0 to about 75% of a volatile liquid diluent.

For agronomic applications, the rate of application required for effective control (i.e. "biologically effective amount") will depend on such factors as the species of nematode to be controlled, the nematode's life cycle, life stage, its size, location, time of year, host crop or animal, feeding behavior, mating behavior, ambient moisture, temperature, and the like. Under normal circumstances, application rates of about 0.01 to 2 kg of active ingredients per hectare are sufficient to control nematodes in agronomic ecosystems, but as little as 0.0001 kg/hectare may be sufficient or as much as 8 kg/hectare may be required. For nonagronomic applications, effective use rates will range from about 1.0 to 50 mg/square meter but as little as 0.1 mg/square meter may be sufficient or as much as 150 mg/square meter may be required. One skilled in the art can easily determine the biologically effective amount necessary for the desired level of parasitic nematode control.

The following Tests demonstrate the control efficacy of compounds of this invention on specific pests. "Control efficacy" represents inhibition of parasitic nematode development (including mortality) that causes significantly reduced feeding. The pest control protection afforded by the compounds is not limited, however, to these species.

BIOLOGICAL EXAMPLES OF THE INVENTION

Test A

Control of the southern root-knot nematode (Meloidogyne incognita) through contact and/or systemic means was evaluated in test units consisting of small open containers filled with a sandy soil mixture and cucumber seedlings.

Test compounds were formulated using a solution containing 50% acetone and 50% water. Test compounds were applied directly to the soil of the test units at concentrations of 500 ppm active ingredient. Each test was replicated 3 times. After treatment, the test units were allowed to dry for 1 hour, after which time about 400 second-stage juvenile (J2) larvae and 800 eggs were pipetted into the soil. The test units were held at 27° C. and watered as needed for 7 days.

Nematocidal efficacy was determined by the amount of root gall formation observed when compared to an untreated control. No gall formation was indicative of 100% nematode control. Gall formation equivalent to that found in the untreated control was indicative of 0% control. No nematode control rating was given to compounds showing significant phytotoxicity.

Of the compounds tested at a concentration of 500 ppm, the following provided good levels of plant protection (50% or more reduction in root galling, compared to solvent-treated controls) and exhibited no significant phytotoxicity: 1, 2, 3, 4, 5, 6, 7, 8, 10, 11, 12, 14, 16, 17, 18, 19, 20, 21, 22, 23, 24, 26, 27, 29, 30, 32, 33, 34, 35, 36, 37, 39, 40, 42, 43, 45, 46, 47, 48, 50, 52, 53, 56, 58, 60, 62, 63, 65, 67, 70, 72, 74, 75, 77, 80, 89, 90, 92, 95, 96, 101 and 103.

What is claimed is:

1. A compound selected from Formula 1 when used as a nematocide,

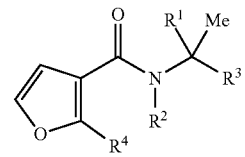

wherein
$R^1$ is H or methyl;
$R^2$ is H; or $C_1$-$C_6$ alkyl, $C_2$-$C_6$ alkenyl, $C_2$-$C_6$ alkynyl, $C_3$-$C_6$ cycloalkyl, $C_2$-$C_6$ alkylcarbonyl, $C_2$-$C_6$ alkoxycarbonyl, $C_1$-$C_6$ alkylthio or $C_1$-$C_6$ alkylsulfonyl, each unsubstituted or substituted with at least one $R^5$;
$R^3$ is $C_2$-$C_{16}$ alkyl, $C_2$-$C_{16}$ alkenyl, $C_2$-$C_{16}$ alkynyl or $C_3$-$C_6$ cycloalkyl, each unsubstituted or substituted with at least one $R^6$;
$R^4$ is Cl or Br;
each $R^5$ is independently halogen, cyano, $C_1$-$C_3$ alkoxy, $C_3$-$C_6$ cycloalkyl, $C_1$-$C_3$ alkylthio, $C_1$-$C_3$ alkylsulfinyl or $C_1$-$C_3$ alkylsulfonyl;
each $R^6$ is independently halogen, cyano, $C_1$-$C_3$ alkoxy, $C_3$-$C_6$ cycloalkyl, $C_1$-$C_3$ alkylthio, $C_1$-$C_3$ alkylsulfinyl, $C_1$-$C_3$ alkylsulfonyl or $SiR^aR^bR^c$; and
each $R^a$, $R^b$ and $R^c$ is independently $C_1$-$C_6$ alkyl;
provided that (i) when $R^1$ and $R^2$ are H, then $R^3$ is other than $C_2$-$C_3$ alkenyl, $C_2$-$C_3$ alkynyl, cyclopropyl, —$CH_2OCH_3$, —$CH_2SCH_3$, unsubstituted $C_2$-$C_3$ alkyl, or $C_2$-$C_3$ alkyl substituted with Cl or Br (ii) when $R^1$ is methyl, then $R^3$ is other than ethyl; and (iii) when $R^1$ is H and $R^2$ is methyl, then $R^3$ is other than ethyl.

2. A compound selected from Formula 1a when used as a nematocide,

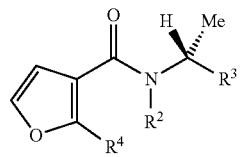

wherein
$R^2$ is H; or $C_1$-$C_6$ alkyl, $C_2$-$C_6$ alkenyl, $C_2$-$C_6$ alkynyl, $C_3$-$C_6$ cycloalkyl, $C_2$-$C_6$ alkylcarbonyl, $C_2$-$C_6$ alkoxycarbonyl, $C_1$-$C_6$ alkylthio or $C_1$-$C_6$ alkylsulfonyl, each unsubstituted or substituted with at least one $R^5$;

R$^3$ is C$_2$-C$_{16}$ alkyl, C$_2$-C$_{16}$ alkenyl, C$_2$-C$_{16}$ alkynyl or C$_3$-C$_6$ cycloalkyl, each unsubstituted or substituted with at least one R$^6$;

R$^4$ is Cl, Br, I, CF$_3$ or cyano;

each R$^5$ is independently halogen, cyano, C$_1$-C$_3$ alkoxy, C$_3$-C$_6$ cycloalkyl, C$_1$-C$_3$ alkylthio, C$_1$-C$_3$ alkylsulfinyl or C$_1$-C$_3$ alkylsulfonyl;

each R$^6$ is independently halogen, cyano, C$_1$-C$_3$ alkoxy, C$_3$-C$_6$ cycloalkyl, C$_1$-C$_3$ alkylthio, C$_1$-C$_3$ alkylsulfinyl, C$_1$-C$_3$ alkylsulfonyl or SiR$^a$R$^b$R$^c$; and each R$^a$, R$^b$ and R$^c$ is independently C$_1$-C$_6$ alkyl.

3. A compound selected from Formula 1b when used as a nematocide,

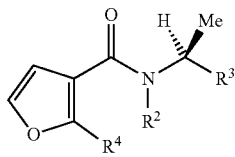

wherein
R$^2$ is H; or C$_1$-C$_6$ alkyl, C$_2$-C$_6$ alkenyl, C$_2$-C$_6$ alkynyl, C$_3$-C$_6$ cycloalkyl, C$_2$-C$_6$ alkylcarbonyl, C$_2$-C$_6$ alkoxycarbonyl, C$_1$-C$_6$ alkylthio or C$_1$-C$_6$ alkylsulfonyl, each unsubstituted or substituted with at least one R$^5$;

R$^3$ is C$_2$-C$_{16}$ alkyl, C$_2$-C$_{16}$ alkenyl, C$_2$-C$_{16}$ alkynyl or C$_3$-C$_6$ cycloalkyl, each unsubstituted or substituted with at least one R$^6$;

R$^4$ is Cl, Br, I, CF$_3$ or cyano;

each R$^5$ is independently halogen, cyano, C$_1$-C$_3$ alkoxy, C$_3$-C$_6$ cycloalkyl, C$_1$-C$_3$ alkylthio, C$_1$-C$_3$ alkylsulfinyl or C$_1$-C$_3$ alkylsulfonyl;

each R$^6$ is independently halogen, cyano, C$_1$-C$_3$ alkoxy, C$_3$-C$_6$ cycloalkyl, C$_1$-C$_3$ alkylthio, C$_1$-C$_3$ alkylsulfinyl, C$_1$-C$_3$ alkylsulfonyl or SiR$^a$R$^b$R$^c$; and each R$^a$, R$^b$ and R$^c$ is independently C$_1$-C$_6$ alkyl.

4. A composition comprising a compound of claim 1, and at least one additional component selected from the group consisting of surfactants, solid diluents and liquid diluents, said composition optionally further comprising at least one additional biologically active compound or agent.

5. The composition of claim 4 wherein the at least one additional biologically active compound or agent is selected from the group consisting of abamectin, acephate, acequinocyl, acetamiprid, acrinathrin, afidopyropen, amidoflumet, amitraz, avermectin, azadirachtin, azinphos-methyl, benfuracarb, bensultap, bifenthrin, bifenazate, bistrifluron, borate, buprofezin, cadusafos, carbaryl, carbofuran, cartap, carzol, chlorantraniliprole, chlorfenapyr, chlorfluazuron, chlorpyrifos, chlorpyrifos-methyl, chromafenozide, clofentezin, clothianidin, cyantraniliprole, cyanliliprole, cyproprothrin, cycloxaprid, cyflumetofen, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, diafenthiuron, diazinon, dieldrin, diflubenzuron, dimefluthrin, dimehypo, dimethoate, dinotefuran, diofenolan, emamectin, endosulfan, esfenvalerate, ethiprole, etofenprox, etoxazole, fenbutatin oxide, fenitrothion, fenothiocarb, fenoxycarb, fenpropathrin, fenvalerate, fipronil, flometoquin, flonicamid, flubendiamide, flucythrinate, flufenerim, flufenoxuron, flufenoxystrobin, fluensulfone, fluopyram, flupyradifurone, fluvalinate, tau-fluvalinate, fonophos, formetanate, fosthiazate, halofenozide, heptafluthrin, hexaflumuron, hexythiazox, hydramethylnon, imidacloprid, indoxacarb, insecticidal soaps, isofenphos, lufenuron, malathion, meperfluthrin, metaflumizone, metaldehyde, methamidophos, methidathion, methiocarb, methomyl, methoprene, methoxychlor, methoxyfenozide, metofluthrin, monocrotophos, monofluorothrin, nicotine, nitenpyram, nithiazine, novaluron, noviflumuron, oxamyl, parathion, parathion-methyl, permethrin, phorate, phosalone, phosmet, phosphamidon, pirimicarb, profenofos, profluthrin, propargite, protrifenbute, pyflubumide, pymetrozine, pyrafluprole, pyrethrin, pyridaben, pyridalyl, pyrifluquinazon, pyriminostrobin, pyriprole, pyriproxyfen, rotenone, ryanodine, silafluofen, spinetoram, spinosad, spirodiclofen, spiromesifen, spirotetramat, sulprofos, sulfoxaflor, tebufenozide, tebufenpyrad, teflubenzuron, tefluthrin, terbufos, tetrachlorvinphos, tetramethrin, tetramethylfluthrin, thiacloprid, thiamethoxam, thiodicarb, thiosultap-sodium, tioxazafen, tolfenpyrad, tralomethrin, triazamate, trichlorfon, triflumezopyrim, triflumuron, *Bacillus thuringiensis* delta-endotoxins, entomopathogenic bacteria, entomopathogenic viruses and entomopathogenic fungi.

6. The composition of claim 5 wherein the at least one additional biologically active compound or agent is selected from the group consisting of abamectin, acetamiprid, acrinathrin, afidopyropen, amitraz, avermectin, azadirachtin, benfuracarb, bensultap, bifenthrin, buprofezin, cadusafos, carbaryl, cartap, chlorantraniliprole, chlorfenapyr, chlorpyrifos, clothianidin, cyantraniliprole, cyanliliprole, cycloprothrin, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, dieldrin, dinotefuran, diofenolan, emamectin, endosulfan, esfenvalerate, ethiprole, etofenprox, etoxazole, fenitrothion, fenothiocarb, fenoxycarb, fenvalerate, fipronil, flometoquin, flonicamid, flubendiamide, flufenoxuron, flufenoxystrobin, fluensulfone, flupiprole, flupyradifurone, fluvalinate, formetanate, fosthiazate, heptafluthrin, hexaflumuron, hydramethylnon, imidacloprid, indoxacarb, lufenuron, meperfluthrin, metaflumizone, methiocarb, methomyl, methoprene, methoxyfenozide, metofluthrin, monofluorothrin, nitenpyram, nithiazine, novaluron, oxamyl, pyflubumide, pymetrozine, pyrethrin, pyridaben, pyridalyl, pyriminostrobin, pyriproxyfen, ryanodine, spinetoram, spinosad, spirodiclofen, spiromesifen, spirotetramat, sulfoxaflor, tebufenozide, tetramethrin, tetramethylfluthrin, thiacloprid, thiamethoxam, thiodicarb, thiosultap-sodium, tralomethrin, triazamate, triflumezopyrim, triflumuron, *Bacillus thuringiensis* delta-endotoxins, all strains of *Bacillus thuringiensis* and all strains of nucleo polyhedrosis viruses.

7. A treated seed comprising the compound of claim 1, in an amount of from about 0.0001 to 1% by weight of the seed before treatment.

8. A composition comprising (i) a compound of Formula 1a and a compound of Formula 1b,

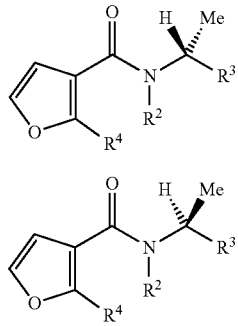

wherein the ratio of 1b to 1a is at least 55:45; and wherein $R^2$ is H; or $C_1$-$C_6$ alkyl, $C_2$-$C_6$ alkenyl, $C_2$-$C_6$ alkynyl, $C_3$-$C_6$ cycloalkyl, $C_2$-$C_6$ alkylcarbonyl, $C_2$-$C_6$ alkoxycarbonyl, $C_1$-$C_6$ alkylthio or $C_1$-$C_6$ alkylsulfonyl, each unsubstituted or substituted with at least one $R^5$;

$R^3$ is $C_2$-$C_{16}$ alkyl, $C_2$-$C_{16}$ alkenyl, $C_2$-$C_{16}$ alkynyl or $C_3$-$C_6$ cycloalkyl, each unsubstituted or substituted with at least one $R^6$;

$R^4$ is Cl, Br, I, $CF_3$ or cyano;

each $R^5$ is independently halogen, cyano, $C_1$-$C_3$ alkoxy, $C_3$-$C_6$ cycloalkyl, $C_1$-$C_3$ alkylthio, $C_1$-$C_3$ alkylsulfinyl or $C_1$-$C_3$ alkylsulfonyl;

each $R^6$ is independently halogen, cyano, $C_1$-$C_3$ alkoxy, $C_3$-$C_6$ cycloalkyl, $C_1$-$C_3$ alkylthio, $C_1$-$C_3$ alkylsulfinyl, $C_1$-$C_3$ alkylsulfonyl or $SiR^aR^bR^c$; and each $R^a$, $R^b$ and $R^c$ is independently $C_1$-$C_6$ alkyl; and (ii) at least one additional component selected from the group consisting of surfactants, solid diluents and liquid diluents.

9. The composition of claim 8 wherein the compound of Formula 1b is present in a nematocidally effective amount.

10. A method for controlling a soil-dwelling nematode comprising contacting the nematode or its environment with a biologically effective amount of the composition of claim 8.

* * * * *